United States Patent [19]
Labrie et al.

[11] Patent Number: 6,124,115
[45] Date of Patent: Sep. 26, 2000

[54] PRODUCTION AND USE OF ISOLATED TYPE 5 17β-HYDROXYSTEROID DEHYDROGENASE

[75] Inventors: Fernand Labrie, Ste-Foy; Van Luu-The, Charny, both of Canada

[73] Assignee: Endorecherche Inc., Canada

[*] Notice: This patent issued on a continued prosecution application filed under 37 CFR 1.53(d), and is subject to the twenty year patent term provisions of 35 U.S.C. 154(a)(2).

[21] Appl. No.: 08/532,896

[22] Filed: Sep. 22, 1995

[51] Int. Cl.[7] .............................. C12N 5/10; C12N 15/09; C12N 15/12; C12N 15/63
[52] U.S. Cl. .................... 435/69.1; 435/320.1; 435/325; 536/23.2
[58] Field of Search .............................. 435/6, 69.1, 70.1, 435/70.3, 91.1, 183, 320.1, 172.3, 455, 463, 466; 536/23.1, 23.2, 23.5; 935/9, 66

[56] References Cited

PUBLICATIONS

Luu–The, V. et al., *Mol. Endocrinol.*, 3:1301–1309 (1989).
Peltoketo, H. et al., *FEBS Lett*, 239:73–77 (1988).
Wu, L. et al., *J. Biol Chem*, 268:12964–12969 (1993).
Geissler, WM, *Nature Genetics*, 7:34–39 (1994).
Hélène et al., *Biochimica et Biophysica Acta*, 1049:99–125 (1990).
Maniatis in Molecular Cloning: A Laboratory Manual (Cold Spring Harbor Press 1982); pp. 1.21–1.41.
Sanger F. et al., *Proc. Natl. Acad. Sci.*, 74:5463–5467 (1977).
Kingston, R.E., In: Current Protocols in Molecular Biology, Ausubel et al. eds., pp. 9.1.1–9.1.9, John Wiley & Sons, N.Y. (1987).
Lachance et al., *J. Biol. Chem.*, 265:20469–20475 (1990).
Lachance et al., *DNA and Cell Biol.* 10:701–711 (1991).
Bernier et al., *J. Biol. Chem*, 269, 28200–28205, (1994).
Deyashiki, et al. *J. Biol. Chem*, 270, 10461–10467, (1995).
Zhang, et al., *Clinical and Investigative Medicine*, 18(4):b40 XP000196659 (1995).
Miyajima, *EMBL Sequence Data*, Human m RNA (HA1753), Abs. XP002020808 (1993).
Qin, et al., *J. Steroid Biochem. and Molecular Biology*, 46:673–679 (1993).
Luu–The, et al., *J. Steroid Biochem. and Molecular Biology*, 55(5–6):581–587 (1995).
Labrie, et al., *J. Steroid Biochem.*, 34(1–6):189–197 (1989).
Dumont, et al., *J. Steroid Biochem. and Molecular Biology*, 41(3–8):605–608 (1992).
Peltoketo, et al., *European Journal of Biochemistry*, 209(1):459–466 (1992).
Andersson, et al., *J. Steroid Biochem. and Molecular Biology*, 53(1–6):37–39 (1995).
Rothenberg, et al., *J. National Cancer Institute*, 81(20):39–44 (1989).
Ciaccio, et al., *EMBL Sequence Database*, Human dihydrodiol dehydrogenase gene, 5'–flanking region, Abs. XP002020809 (1996).

*Primary Examiner*—Robert A. Schwartzman
*Assistant Examiner*—Thomas G. Larson
*Attorney, Agent, or Firm*—Ostrolenk, Faber, Gerb & Soffen, LLP

[57] ABSTRACT

A novel type 5 17β-hydroxysteroid dehydrogenase is provided. Methods of producing the enzyme and using the enzyme to identify potential compounds which inhibit or alter the activity of the enzyme are described. In addition, methods of using the gene sequence or portions thereof for probes or to produce expression-disrupting sense or antisense DNA fragments thereof, or antisense RNA, are provided.

12 Claims, 13 Drawing Sheets

```
GTGACAGGGA ATG GAT TCC AAA CAG CAG TGT GTA AAG CTA AAT GAT GGC
           Met Asp Ser Lys Gln Gln Cys Val Lys Leu Asn Asp Gly    49

CAC TTC ATG CCT GTA TTG GGA TTT GGC ACC TAT GCA CCT CCA GAG GTT
His Phe Met Pro Val Leu Gly Phe Gly Thr Tyr Ala Pro Pro Glu Val   97

CCG AGA AGT AAA GCT TTG GAG GTC ACC AAA TTA GCA ATA GAA GCT GGG
Pro Arg Ser Lys Ala Leu Glu Val Thr Lys Leu Ala Ile Glu Ala Gly  145

TTC CGC CAT ATA GAT TCT GCT CAT TTA TAC AAT AAT GAG GAG CAG GTT
Phe Arg His Ile Asp Ser Ala His Leu Tyr Asn Asn Glu Glu Gln Val  193
                                      TSK

GGA CTG GCC ATC CGA AGC AAG ATT GCA GAT GGC AGT GTG AAG AGA GAA
Gly Leu Ala Ile Arg Ser Lys Ile Ala Asp Gly Ser Val Lys Arg Glu  241
                                                PKC

GAC ATA TTC TAC ACT TCA AAG CTT TGG TCC ACT TTT CAT CGA CCA GAG
Asp Ile Phe Tyr Thr Ser Lys Leu Trp Ser Thr Phe His Arg Pro Glu  289
              PKC

TTG GTC CGA CCA GCC TTG GAA AAC TCA CTG AAA GCT CAA TTG GAC
Leu Val Arg Pro Ala Leu Glu Asn Ser Leu Lys Ala Gln Leu Asp      337
```

```
TAT GTT GAC CTC TAT CTT ATT CAT TCT CCA ATG TCT CTA AAG CCA GGT   385
Tyr Val Asp Leu Tyr Leu Ile His Ser Pro Met Ser Leu Lys Pro Gly
                                        Ser
                                        PKC

GAG GAA CTT TCA CCA ACA GAT GAA AAT GGA AAA GTA ATA TTT GAC ATA   433
Glu Glu Leu Ser Pro Thr Asp Glu Asn Gly Lys Val Ile Phe Asp Ile
        Ser
        CK2

GTG GAT CTC TGT AAG GAT GCA ATG GAG GCC ATG GAG AAG TGT AAG GAT GCA   481
Val Asp Leu Cys Lys Asp Ala Met Glu Ala Met Glu Lys Cys Lys Asp Ala
        Thr
        CK2

GGA TTG GCC AAG TCC ATT GGG GTG TCA AAC TTC AAC CGC AGG CAG CTG   529
Gly Leu Ala Lys Ser Ile Gly Val Ser Asn Phe Asn Arg Arg Gln Leu
                        Gly Val Ser Asn Phe
NM Aldo/Keto reductase family signature 1

GAG ATG ATC CTC AAC AAG CCA GGA CTC AAG TAC AAG CCT GTC TGC AAC   577
Glu Met Ile Leu Asn Lys Pro Gly Leu Lys Tyr Lys Pro Val Cys Asn
                            Asn
                            NG

CAG GTA GAA TGT CAT CCG TAT TTC AAC CGG AGT AAA TTG CTA GAT TTC   625
Gln Val Glu Cys His Pro Tyr Phe Asn Arg Ser Lys Leu Leu Asp Phe

TGC AAG TCG AAA GAT ATT GTT CTG GTT GCC TAT AGT GCT CTG GGA TCT   673
Cys Lys Ser Lys Asp Ile Val Leu Val Ala Tyr Ser Ala Leu Gly Ser
                                                            Ser
                                                            PKC

CAA CGA GAC AAA CGA TGG GTG GAC CCG AAC TCC CCG GTG CTC TTG GAG   721
Gln Arg Asp Lys Arg Trp Val Asp Pro Asn Ser Pro Val Leu Leu Glu
```

```
GAC CCA GTC CTT TGT GCC TTG GCA AAA AAG CAC AAG CGA ACC CCA GCC    769
Asp Pro Val Leu Cys Ala Leu Ala Lys Lys His Lys Arg Thr Pro Ala

CTG ATT GCC CTG CGC TAC CAG CTG CAG CGT GGG GTT GTG GTC CTG GCC    817
Leu Ile Ala Leu Arg Tyr Gln Leu Gln Arg Gly Val Val Val Leu Ala
                                        Aldo/Keto reductase family
AAG AGC TAC AAT GAG CAG CGC ATC AGA GAT GCC ATA GAT GGC CTA GAC AGA 865
Lys Ser Tyr Asn Glu Gln Arg Ile Arg Asp Ala Ile Asp Gly Leu Asp Arg
        CK2 signature 2                                        NM
TTC CAG TTG ACT GCA GAG GAC ATG AAA GCC GAG GTG CAG GTT TTT GAG    913
Phe Gln Leu Thr Ala Glu Asp Met Lys Ala Glu Val Gln Val Phe Glu AAT CTC CAC TAT TTT AAC AGT GAT AGT TTT GCT AGC CAC CCT AAT TAT    961
Asn Leu His Tyr Phe Asn Ser Asp Ser Phe Ala Ser His Pro Asn Tyr CCA TAT TCA GAT GAA TAT TAA CATGGAGACT TTGCCTGATG ATGTCTACCA      1012
Pro Tyr Ser Asp Glu Tyr *

GAAGGCCCTG TGTGTGGATG GTGACGCAGA GGACGTCTCT ATGCCGGTGA CTGGACATAT 1072
CACCTCTACT TAAATCCGTC CTGTTTAGCG ACTTCAGTCA ACTACAGCTC ACTCCATAGG 1132
CCAGAAATAC AATAAATCCT GTTTAGCGAC TTCAGTCAAC TACAGCTCAC TCCATAGGCC 1192
AGAAATACAA TAAA                                                  1206
```

FIG. 3C

```
AAGAACAAATACTATTAAGGCACTGCTTGCATATATTAAATGATGTCCAAACTGTTAATAATTAACACTCC
AATAAAAACTACACCAGAATTTCTTTTTATTTGCACCTCATCAGACTTTATCAGGACTGCATCTCTTCAGA
AATGAATATTTCTCTACAACGCAAAGAAAATCAAAATAAATTTCTGATTGAAAATGTAAAAGGCAAATATT
TTACAGTTTTTAACTTTAATTTTTTATTGAGAGACCAACTGTGTTGAAAAATTTCATTAGTCATTCCTTAAATTATGTGTA
TGTGAGAAAGACGTAAGATGGTTTTTATATGTCTAACATATGTTGTTCTACAAATCCTTTTGAATAATTAAT
AAAGATATTTGTAGCTGGAGTTTTTATATGTCTAACATATGTTGTTCTACAAATCCTTTTGAATAATTAAT
ATAGAGATTTCGAATAGAAAAATAACTTTAGATAGAAATTAGTGAGTTTATTATAACCATATATTATAATTACTT
AGGAATTCTCTTTGATAAGAAGAACAAATGAACTGCAATTTCTCCACAGACCAATATAAGACTGCCTATGTACCTCCT
CCTACACATGCCCATTGGTTAACCATCAGTTGCAGGGGTGCAGGGGTTTCCTGCCCATTGTTTTTGTAATCTCT
GAGGAAGC

AGCAGCAAACATTGCTAGTCAGACAAGTGACAGGA
Met Asp Ser Lys Gln Gln Cys Val Lys Leu Asn Asp Gly His Phe Met Pro Val Leu Gly
ATG GAT TCC AAA CAG CAG TGT GTA AAG CTA AAT GAT GGC CAC TTC ATG CCT GTA TTG GGA
Phe Gly Thr Tyr Ala Pro Pro Glu
TTT GGC ACC TAT GCA CCT CCA GAG

GTAAGAATAATTCCTTTTAGTTTTCGGATTTCAAAAGAATAAACCTAGTAGAAGTGAAACCCTATTGGGTTGTAAGGTT
CGTGTTCCTACCTTACTCTGGATGACTCACTGGTCGCTGTTATTGGTGCAATCCTTGTCTG
CATTGAGGTCCATTCCTACTGTGCACTGTTTCTTCTCGTTCATGTCAGTTC
CCAGCTTGGCAG........1.2 kb.........GGAAGTCTGAGTGAGCATTCTGTTAATATCACTGGAGAG
AACTCATATGAGCTGCACCGTTTCCCTTCTATACTCCATGTGATTTTACCATGTATATCACTATATTAAAATAA
TTAGGACTATTTCAGTCATGTCATTGTTAACTTTTCCAACAAATCACTGAGGTGTTATGTGTACCTCCATAACAGTGA
TCAACAGATTGCCTGAGACTTTATTACTAACCAGGAAAGACTCAGGCAAAC
TGAGATGGACTTTTCACCCCACAGAGGAGAAAAGCTGATTCTTGTATAAAAGTCAATGCTGTGCCTGAACTA
CCTCTCAGCCACAGTGATCACCAGATACTACCTTTGGTTGCTCCTCCAG
```

FIG. 5A-1

```
Val Pro Arg Ser Lys Ala Leu Glu Val Thr Lys Leu Ala Ile Glu Ala Gly Phe Arg His   48
GTT CCG AGA AGT AAA GCT TTG GAG GTC ACA AAA TTA GCA ATA GAA GCT GGG TTC CGC CAT

Ile Asp Ser Ala His Leu Tyr Asn Glu Gln Val Gly Leu Ala Ile Arg Ser Lys           68
ATA GAT TCT GCT CAT TTA TAC AAT GAG CAG GTT GGA CTG GCC ATC CGA AGC AAG

Ile Ala Asp Gly Ser Val Lys Arg Glu Asp Ile Phe Tyr Thr Ser Lys                   84
ATT GCA GAT GGC AGT GTG AAG AGA GAA GAC ATA TTC TAC ACT TCA AAG

GTACTGTGTCTATGATGAGCTTGTGTGCACATGTATTTATTGTGATTGTGTGGAGATGACAATTCTATGACTGGATGAGT
AGTTGTGGGTGAATTTGCTTCTGGGTTGTGTGTCAAATTTATTCACACATACTAAAACTGAAATCAAAATCAAGGAA
TGATGATCACTTTTCATTTTGGCTGTGTGTTCCAATTTATGACCTGAAAGTCCCTTACTTTTTGAGCTTCAGCCGAGATC
AGTGTGATTTGACATGTGCTATAGAATCACAGAGAACAATAATCATGTTATGTTTTTCTTATCGCCTGGGTGATTTCT
AAGATTTCTTATTATTCTCAATTGCTATCTTTATCAGTGAGATAGAAGCAATATAAGAAAGCTCTGGAGTATTAAA
TAATAGACACTTAAATTGTCCTAAATTGTGTCCAGCATAGTGAGCATGTTCAAAACTTGTTTTACCCCCCTTTTATGTTG
CTTTAGTTTCTAAGCAACATAAATAGCTATTCTTAAGCATCATAGTTATTACTTAATAATCTTACATTTTAAGAATTACTCC
TGTAAACTCTGAAGATGTACAAACTATACATCCAAGTTATTACTTAATAATCTATATAAGTTTATAAGGATAGG......0.1 kb......
TATCATTCAGTAGATGTACAAACTATACATCCAAGTTATTACTTAATAATCTATATAAGTTTATAAGGATAGG
ACTAGATGCACAAAGTAATAAGAGATTTGCTCAAGCATTCATTCAAAATCACCTCCATTCTTTAACCTCTGCAG
```

FIG. 5A-2

```
Leu Trp Ser Thr Phe His Arg Pro Glu Leu Val Arg Pro Ala Leu Glu Asn Ser Leu Lys   104
CTT TGG TCC ACT TTT CAT CGA CCA GAG TTG GTC CGA GCC TTG GAA AAC TCA CTG AAA
Lys Ala Gln Leu Asp Tyr Val Asp Leu Tyr Leu His Ser Pro Met Ser Leu Lys           123
AAA GCT CAA TTG GAC TAT GTT GAC CTC TAT CTT CAT TCT CCA ATG TCT CTA AAG

GTATGCAGTTTGTATGAGCATAAAATTGCGCTTCTCTGCTGTCATTATAAACATTGTTTATCTGGATAGTTGAACAGAGCTT
TTTATTAGGAGGATGTAGGGATTATCACACAGAAGAAGATTGGAACACCTAAGTTCCTTTCTTTC........
0.9 kb........ATATAATATTTGTAAGAGATTAGAGAAGCCTGTCTCCTGAATACATTCCTATACCTTCATAT
GTAAAACACTTAGCACATATCACTTTCTGGAGCATTGTACCACCTGTGTCTCATGGAGGATTAGTGTCCTTAAAGGTACCTG
GGGTTACAGCTATGAGTGGAGAAATTAAATTGTGACATCATTAAAATGACTGCTTCTATTTCAG

Pro Gly Glu Glu Leu Ser Pro Thr Asp Glu Asn Gly Lys Val Ile Phe Asp Ile Val Asp   143
CCA GGT GAG GAG CTT TCA CCA ACA GAT GAA AAT GGA AAA GTA ATA TTT GAC ATA GTG GAT
Leu Cys Thr Thr Trp Glu                                                           149
CTC TGT ACC ACC TGG GAG

GTGAGTGCTGCTTGGCGGAGAGGAGACACAGAGAAGGATGACAAAAAGAGAAAATCTGTTTCCCAGGTTCGATAGGAAAGAATGG
AATATGCACCATTAGATC.......GACAGGAATCTCTTCTTCTGTGCTTGCTGCTGTTTGCTGTCTGTTGCATTAATCTAT
GCAGTTCCTAAGGAAGAGATAGAAATTCTTACTTCTTGCCTGCCCTATTGCTGCTGTTGCATTTGAATTTTCT
TTTTTGACAATCATCACTGCTAGCTATTTCATTGTCATATCTTGAAAGTGTCCCTCACAGTTGCTGTCTTGCATTTACC
GTGATTGCAGCCAACTGCACAAATAATTCCTCACAACCCCTTTCTCCACAG
```

FIG. 5A-3

```
Ala Met Glu Lys Cys Lys Asp Ala Gly Leu Ala Lys Ser Ile Gly Val Ser Asn Phe Asn    169
GCC ATG GAG AAG TGT AAG GAT GCA GGA TTG GCC AAG TCC ATT GGG GTG TCA AAC TTC AAC
Arg Arg Gln Leu Glu Met Ile Leu Asn Lys Pro Gly Leu Lys Tyr Lys Pro Val Cys Asn    189
CGC AGG CAG CTG GAG ATG ATC CTC AAC AAG CCA GGA CTC AAG TAC AAG CCT GTC TGC AAC
Gln                                                                                 190
CAG

GTGAGCTCCCTTGGCCTTCTCTCCTTTCGGTTCTTCATGCCCCCTCTTCCTGTCCTATTGCCAAATATCTGTTTGTTTT
GTCCCAGTTATCTTTGTGAAGTAGAGAGCAAGCTTCTGTCAAGAAA...........2.8 kb
............ATTTCCATTTATACTTTTAGAAGATATAAAATTTATTTCTATGAAAAAGGTTATT
ACTTGACAATAATATCCTCAGCTCAAATATAATGCTATACTGATTATTATTCAGCTTCCTTACTTTCATCTTTTCAATA
TTAACATAAACTATTTCATATAAATTGATGCTTCTCTCTTTTGGTCAACTGCAG

Val Glu Cys His Pro Tyr Phe Asn Arg Ser Lys Leu Leu Asp Phe Cys Lys Ser Lys Asp    210
GTA GAA TGT CAT CCG TAT TTC AAC CGG AGT AAA TTG CTA GAT TTC TGC AAG TCG AAA GAT
Ile Val Leu Val Ala Tyr Ser Ala Leu Gly Ser Gln Arg Asp Lys Arg Tr                  227
ATT GTT CTG GTT GCC TAT AGT GCT CTG GGA TCT CAA CGA GAC AAA CGA TG

GTAATAAAAACAATGGGACCTTTACATAAACCTTCATTTGCAGAAATTTTTAGTCAGAGCATCCTCAGTTTCCTGT
AGTTAAGTTTCAAGTGGCTCATGGAGGAGAAAGAGAATTGCGTTTCTGACGAGATCT..........0.1 kb...
....TTTAGGGAGCTGCCTAACAAACTATCGGCAGCCTCAGGGCCTTCAGCCTTTCTGCCTTTCCTTCCAG
```

FIG. 5B-1

```
p Val Asp Pro Asn Ser Pro Val Leu Leu Glu Asp Pro Val Leu Cys Ala Leu Ala Lys    246
G GTG GAC CCG AAC TCC CCG GTG CTC TTG GAG GAC CCA GTC CTT TGT GCC TTG GCA AAA
Lys His Lys Arg Thr Pro Ala Leu Ile Ala Leu Arg Tyr Gln Leu Gln Arg Gly Val Val    266
AAG CAC AAG CGA ACC CCA GCC CTG ATT GCC CTG CGC TAC CAG CTG CAG CGT GGG GTT GTG
Val Leu Ala Lys Ser Tyr Asn Glu Arg Ile Arg Gln Asn Val Gln                        282
GTC CTG GCC AAG AGC TAC AAT GAG CGC ATC AGA CAG AAC GTG CAG

GTGAGGAGCGGGGGCTGTGGGCCTCAGGTCTCTCCTGCACAGTGTCCTTCACACGTGTGCTTCTTGTAAGGCTCTCAGGACA
GCCTTGGGCCAGCTCCCAGTTCCCCTGTATTCCCATATGAATGCTTGCCTGCATCCT........2.5.......
.........CCCTATCATGTGGGCACAATGTCAGCGCTGTTCTCTCCATTTCTCGTTGAAATTTCTCTTGTCTGC
AGAGTTGCACAGTTTCAATACATAAGAATGGATTCTGCTTATTTTTCGTGAGCTATTCATTGACCACCTG
AGTGTTTAGAGCTGACTTCTATAACTGTTTAAAACTTACCAATATTTTAAGTATTGTCTCTGCACCCTACTGTCTAATA
TACTTGGGGATTCACAACTGCAATCTAAAAATAATAAAGTTTTTATTTCTGATAG

Val Phe Glu Phe Gln Leu Thr Ala Glu Asp Met Lys Ala Ile Asp Gly Leu Asp Arg Asn    302
GTT TTT GAG TTC CAG TTG ACT GCA GAG GAC ATG AAA GCC ATA GAT GGC CTA GAC AGA AAT
Leu His Tyr Phe Asn Ser Asp Se                                                     310
CTC CAC TAT TTT AAC AGT GAT AG
```

FIG. 5B-2

```
GTAAGTTTCCTTTGTAAATGGGTGATCTAATTTATTTCTGGAGAAGGAATGTAGGATGGTGAGAGTGACCTCCATA
CCAGAGGGACAGAGGCCAATGTGAGTCAGAGGTCAGAGTTGAGACTGGAACTCTCCTGCTGACTGGAACTCCAGAGCTCTGTTCTG
GCAGGGTGAGTGGGCAGGGATCAGCAGCATGGGTCAACCTGTCCTGCCTCCATGACTCACTCCATGAACTTTCCAGACAGCC
AACATCATTGCCAAGTCTGCACGTTCCATATAGGCCTGGTGTTTCTACCACTGGACATGCTGTGGATACTGCCATGTGA
CTTCATTAGATGTTCCAAATCTGTCTTATATCACATTGTCCCAAACCTGCTCCTCAGCTCCTTATCAAATCAAAAACATTT
CCATCAACTTTGTGGTCCAGGTGCCAAATTCCCACCTCCTTCATATGGAATGCTTGCTAGATCCTGTCAATTCAGCATCT
TTTATTATTTCAAATGTTTTCCTCCTTCCTTCCTTGCACGTTTGTTCCTGCAATATGGCCCCAAACTCTGCTTTGCCTCCAGAAGCC
TTCCTTAGTGAGTGAATAGGAGTGTGAGTGCTTGGAGGCAGAAGCTCCATTGTTGTATATAATTTGTAGCTGATAAAAGATCT......
..2.7 kb........TTTAATGCACTGTAGCTCCTTCCTTGGATATTAGACCCTATATCATATATAACAATTTACATTTCTG
AATCTTACAAAATATATTGCATACAGTAGGCAGTAGCAGTAATATAAGTAACAAAAGAATATAAATCAGAGTATC
TCTGCTCTGCTGACAGATGTAACAGGAATATACTTGAATATTTGACTTTGTGTTTTACGTGTTTAACTTCCAGATAAGG
AATATGATTGAATTATTATTTTGAAAATACTGTATTATGAAGCCATGTTCATAAAGGTAAGAAAGGCAGATTCTAC
AACTAGTCAGACAACAACTTAACATTCATACTACTAATGACAGCTTCATTGAAATCACTTACTACTCCCCTAGTAATGGAGTCAT
TGCATTTATATTATACATTATATTCTCTTTTCAG r Phe Ala Ser His Pro Asn Tyr Pro Tyr Ser Asp Glu Tyr End
T TTT GCT AGC CAC CCT AAT TAT CCA TAT TCA GAT GAA TAT TAA

CATGGAGGGCTTTGCCTGATGATGTCTACCAGAAGCCCTGTGTGGATGGTGACGCAGAGACGTCTCTATGCCGTG
ACTGGACATATCACCTCTCTACTTAAATCCGTCCTGTTTAGCGACTTCAGTCAACTACAGCTGAGTCCATAGGCCAGAAGA
CAATAAATTTTTATCATTTGAAATAA

TTGAATGTTTTCTCAAAGATTCTTACCTACTCTGTCTCTGTAGTGTGTTTTCTTCTGGCTCAGAAGTGTGTGTGTG
TGTGTGCTTCTTCTGGCTCAACAGGG
```

FIG. 5B-3

PRODUCTION AND USE OF ISOLATED TYPE 5 17β-HYDROXYSTEROID DEHYDROGENASE

BACKGROUND OF THE INVENTION

1. Field of the Invention

The present invention relates to the isolation and characterization of a novel enzyme which is implicated in the production of sex steroids, and more particularly, to the characterization of the gene and cDNA of a novel 20, 17β-hydroxysteroid dehydrogenase (hereinafter type 5 17β-HSD) which has been implicated in the conversion of progesterone and 4-androstenedione ($\Delta^4$-dione) to 20-hydroxyprogesterone (20-OH-P) and testosterone (T), respectively. The use of this enzyme as an assay for inhibitors of the enzyme is also described, as are several other uses of the DNA, fragments thereof and antisense fragments thereof.

2. Description of the Related Art

The enzymes identified as 17β-HSDs are important in the production of human sex steroids, including androst-5-ene-3β,17β-diol ($\Delta^5$-diol), testosterone and estradiol. It was once thought that a single gene encoded a single type of 17β-HSD which was responsible for catalyzing all of the reactions. However, in humans, several types of 17β-HSD have now been identified and characterized. Each type of 17β-HSD has been found to catalyze specific reactions and to be located in specific tissues. Further information about Types 1, 2 and 3 17β-HSD can be had by reference as follows: Type 1 17β-HSD is described by Luu-The, V. et al., *Mol. Endocrinol.*, 3:1301–1309 (1989) and by Peltoketo, H. et al., *FEBSLett*, 239:73–77 (1988); Type 2 17β-HSD is described in Wu, L. et al., *J. Biol Chem*, 268:12964–12969 (1993); Type 3 17β-HSD is described in Geissler, WM, *Nature Genetics*, 7:34–39 (1994). A fourth type which is homologous to porcine ovarian 17β-HSD has recently been identified by researchers Adamski and de Launoit, however, applicant is not presently aware of published information on this type.

The present invention relates to a fifth type of 17β-HSD which is described in detail below.

SUMMARY OF THE INVENTION

It is an object of the present invention to provide a novel 17β-hydroxysteroid dehydrogenase (17β-HSD) which is identified as type 5 17β-HSD.

It is also an object of the present invention to provide a 17β-HSD which has been shown to be involved in the conversion of $\Delta^4$-dione to testosterone and in the conversion of progesterone to 20-hydroxyprogesterone (20-OH-P).

It is a further object of this invention to provide the nucleotide sequences and a gene map for type 5 17β-HSD.

It is also an object of this invention to provide methods of using type 5 17β-HSD in an assay to identify compounds which inhibit the activity of this enzyme, and thus may reduce production of testosterone or 20-hydroxyprogesterone, and can be used to treat medical conditions which respond unfavorably to these steroids.

It is an additional object of this invention to provide methods of preventing the synthesis of type 5 17β-HSD by administering an antisense RNA of the gene sequence of type 5 17β-HSD to interfere with the translation of the gene's mRNA.

These and other objects are discussed herein.

In particular, a novel enzyme, type 5 17β-hydroxysteroid dehydrogenase, has been identified and characterized. The gene sequence for this type 5 17β-HSD was found to encode a protein of 323 amino acids, having an apparent calculated molecular weight of 36,844 daltons. The protein is encoded by nucleotides +11 through 982, including the stop codon (amino acids +1 through 323), numbered in the 5' to 3' direction, in the following sequence (SEQ ID Nos. 1 and 2):

```
GTGACAGGGA ATG GAT TCC AAA CAG CAG TGT GTA AAG CTA AAT GAT GGC         49
           Met Asp Ser Lys Gln Gln Cys Val Lys Leu Asn Asp Gly
            1               5                      10

CAC TTC ATG CCT GTA TTG GGA TTT GGC ACC TAT GCA CCT CCA GAG GTT         97
His Phe Met Pro Val Leu Gly Phe Gly Thr Tyr Ala Pro Pro Glu Val
     15                  20                  25

CCG AGA AGT AAA GCT TTG GAG GTC ACC AAA TTA GCA ATA GAA GCT GGG        145
Pro Arg Ser Lys Ala Leu Glu Val Thr Lys Leu Ala Ile Glu Ala Gly
 30               35                  40                  45

TTC CGC CAT ATA GAT TCT GCT CAT TTA TAC AAT AAT GAG GAG CAG GTT        193
Phe Arg His Ile Asp Ser Ala His Leu Tyr Asn Asn Glu Glu Gln Val
             50                  55                  60

GGA CTG GCC ATC CGA AGC AAG ATT GCA GAT GGC AGT GTG AAG AGA GAA        241
Gly Leu Ala Ile Arg Ser Lys Ile Ala Asp Gly Ser Val Lys Arg Glu
             65                  70                  75

GAC ATA TTC TAC ACT TCA AAG CTT TGG TCC ACT TTT CAT CGA CCA GAG        289
Asp Ile Phe Tyr Thr Ser Lys Leu Trp Ser Thr Phe His Arg Pro Glu
         80                  85                  90

TTG GTC CGA CCA GCC TTG GAA AAC TCA CTG AAA AAA GCT CAA TTG GAC        337
Leu Val Arg Pro Ala Leu Glu Asn Ser Leu Lys Lys Ala Gln Leu Asp
     95                  100                 105

TAT GTT GAC CTC TAT CTT ATT CAT TCT CCA ATG TCT CTA AAG CCA GGT        385
Tyr Val Asp Leu Tyr Leu Ile His Ser Pro Met Ser Leu Lys Pro Gly
110                  115                 120                 125
```

-continued

```
GAG GAA CTT TCA CCA ACA GAT GAA AAT GGA AAA GTA ATA TTT GAC ATA      433
Glu Glu Leu Ser Pro Thr Asp Glu Asn Gly Lys Val Ile Phe Asp Ile
                130                 135                 140

GTG GAT CTC TGT ACC ACC TGG GAG GCC ATG GAG AAG TGT AAG GAT GCA      481
Val Asp Leu Cys Thr Thr Trp Glu Ala Met Glu Lys Cyc Lys Asp Ala
                145                 150                 155

GGA TTG GCC AAG TCC ATT GGG GTG TCA AAC TTC AAC CGC AGG CAG CTG      529
Gly Leu Ala Lys Ser Ile Gly Val Ser Asn Phe Asn Arg Arg Gln Leu
                160                 165                 170

GAG ATG ATC CTC AAC AAG CCA GGA CTC AAG TAC AAG CCT GTC TGC AAC      577
Glu Met Ile Leu Asn Lys Pro Gly Leu Lys Tyr Lys Pro Val Cys Asn
    175                 180                 185

CAG GTA GAA TGT CAT CCG TAT TTC AAC CGG AGT AAA TTG CTA GAT TTC      625
Gln Val Glu Cys His Pro Tyr Phe Asn Arg Ser Lys Leu Leu Asp Phe
190                 195                 200                 205

TGC AAG TCG AAA GAT ATT GTT CTG GTT GCC TAT AGT GCT CTG GGA TCT      673
Cys Lys Ser Lys Asp Ile Val Leu Val Ala Tyr Ser Ala Leu Gly Ser
                210                 215                 220

CAA CGA GAC AAA CGA TGG GTG GAC CCG AAC TCC CCG GTG CTC TTG GAG      721
Gln Arg Asp Lys Arg Trp Val Asp Pro Asn Ser Pro Val Leu Leu Glu
                225                 230                 235

GAC CCA GTC CTT TGT GCC TTG GCA AAA AAG CAC AAG CGA ACC CCA GCC      769
Asp Pro Val Leu Cys Ala Leu Ala Lys Lys His Lys Arg Thr Pro Ala
                240                 245                 250

CTG ATT GCC CTG CGC TAC CAG CTG CAG CGT GGG GTT GTG GTC CTG GCC      817
Leu Ile Ala Leu Arg Tyr Gln Leu Gln Arg Gly Val Val Val Leu Ala
    255                 260                 265

AAG AGC TAC AAT GAG CAG CGC ATC AGA CAG AAC GTG CAG GTT TTT GAG      865
Lys Ser Tyr Asn Glu Gln Arg Ile Arg Gln Asn Val Gln Val Phe Glu
270                 275                 280                 285

TTC CAG TTG ACT GCA GAG GAC ATG AAA GCC ATA GAT GGC CTA GAC AGA      913
Phe Gln Leu Thr Ala Glu Asp Met Lys Ala Ile Asp Gly Leu Asp Arg
                290                 295                 300

AAT CTC CAC TAT TTT AAC AGT GAT AGT TTT GCT AGC CAC CCT AAT TAT      961
Asn Leu His Tyr Phe Asn Ser Asp Ser Phe Ala Ser His Pro Asn Tyr
                305                 310                 315

CCA TAT TCA GAT GAA TAT TAA CATGGAGACT TTGCCTGATGG ATGTCTACCA       1012
Pro Tyr Ser Asp Glu Tyr *
                320

GAAGGCCCTG TGTGTGGATG GTGACGCAGA GGACGTCTCT ATGCCGGTGA CTGGACATAT   1072

CACCTCTACT TAAATCCGTC CTGTTTAGCG ACTTCAGTCA ACTACAGCTC ACTCCATAGG   1132

CCAGAAATAC AATAAATCCT GTTTAGCGAC TTCAGTCAAC TACAGCTCAC TCCATAGGCC   1192

AGAAATACAA TAAA                                                    1206
```

In addition, a complete gene map (FIG. 4) and nucleotide sequences (SEQ. ID Nos. 3 through 29 and FIGS. 5A-1, 5A-2, 5A-3, 5B-1, 5B-2 and 5B-3) of the chromosomal DNA of type 5 17β-HSD are provided. A more detailed description of the sequences will be provided infra.

The present invention includes methods for the synthetic production of type 5 17β-HSD, as well as peptides that are biologically functionally equivalent, and to methods of using these compounds to screen test compounds for their ability to inhibit or alter the enzymatic function. In addition, methods of producing antisense constructs to the type 5 17β-HSD gene's DNA or mRNA or portions thereof, and the use of those antisense constructs to interfere with the transcription or translation of the enzyme are also provided.

The nucleotide sequence which encodes type 5 17β-HSD and recombinant expression vectors which include the sequence may be modified so long as they continue to encode a functionally equivalent enzyme. Moreover, it is contemplated, within the invention, that codons within the coding region may be altered, inter alia, in a manner which, given the degeneracy of the genetic code, continues to encode the same protein or one providing a functionally equivalent protein. It is believed that nucleotide sequences analogous to SEQ ID No. 1, or those that hybridize under stringent conditions to the coding region of SEQ ID No. 1, are likely to encode a type 5 17β-HSD functionally equivalent to that encoded by the coding region of SEQ ID No. 1, especially if such analogous nucleotide sequence is at least 700, preferably at least 850 and most preferably at least 969 nucleotides in length. As used herein, except where otherwise specified, "stringent conditions" means 0.1×SSC (0.3 M sodium chloride and 0.03M sodium citrate) and 0.1% sodium dodecyl sulphate (SDS) and 60° C.

It is also likely that tissues or cells from human or non-human sources and which tissues or cells have the enzymatic machinery to convert $\Delta^4$-dione to testosterone, or to convert progesterone to 20-hydroxyprogesterone, include a type 5 17β-HSD sufficiently analogous to human type 5 17β-HSD to be used in accordance with the present invention. In particular, cDNA libraries prepared from cells performing the foregoing conversions may be screening with probes in accordance with well known techniques prepared by reference to the nucleotides disclosed herein, and under varying degrees of stringency, in order to identify analogous cDNAs in other species. These analogous cDNAs are preferably at least 70% homologous to SEQ ID No. 1, more preferably at least 80% homologous, and most preferably at least 90% homologous. They preferably include stretches of perfect identity at least 10 nucleotides long, more preferably stretches of 15, 20 or even 30 nucleotides of perfect identity. Appropriate probes may be prepared from SEQ ID No. 1 or fragments thereof of suitable length, preferably at least 15 nucleotides in length. Confirmation with at least two distinct probes is preferred. Alternative isolation strategies, such as polymerase chain reaction (PCR) amplification, may also be used.

Homologous type 5 17β-HSDs so obtained, as well as the genes encoding them, are used in accordance with the invention in all of the ways for using SEQ ID No. 2 and SEQ ID No. 1, respectively.

Recombinant expression vectors can include the entire coding region for human type 5 17β-HSD as shown in SEQ ID No. 1, the coding region for human type 5 17β-HSD which has been modified, portions of the coding region for human type 5 17β-HSD, the chromosomal DNA of type 5 17β-HSD, an antisense construct to type 5 17β-HSD, or portions of antisense constructs to type 5 17β-HSD.

In the context of the invention, "isolated" means having a higher purity than exists in nature, but does not require purification from a natural source. Isolated nucleotides encoding type 5 17β-HSD may be produced synthetically, or by isolating cDNA thereof from a cDNA library or by any of numerous other methods well understood in the art.

In one embodiment, the invention provides an isolated nucleotide sequence encoding type 5 17β-hydroxysteroid dehydrogenase, said sequence being sufficiently homologous to SEQ ID No. 1 or a complement thereof, to hybridize under stringent conditions to the coding region of SEQ ID No. 1 or a complement thereof and said sequence encoding an enzyme which catalyzes the conversion of progesterone to 20α-hydroxyprogesterone and the conversion of 4-androstenedione to testosterone.

In a further embodiment, the invention provides an isolated nucleotide sequence comprising at least ten consecutive nucleotides identical to 10 consecutive nucleotides in the coding region of SEQ ID No. 1, or the complement thereof.

In an additional embodiment, the invention provides an oligonucleotide sequence selected from the group consisting of SEQ ID Nos. 30 through 59.

In another embodiment, the invention provides a recombinant expression vector comprising a promoter sequence and an oligonucleotide sequence selected from the group of SEQ ID Nos. 30 to 59.

In a further embodiment, the invention provides a method of blocking synthesis of type 5 17β-HSD, comprising the step of introducing an oligonucleotide selected from the group consisting of SEQ ID Nos. 30 to 59 into cells.

In an additional embodiment, the invention provides an isolated chromosomal DNA fragment which upon transcription and translation encodes type 5 17β-hydroxysteroid dehydrogenase and wherein said fragment contains nine exons and wherein said fragment includes introns which are 16 kilobase pairs in length.

In another embodiment, the invention provides an isolated DNA sequence encoding type 5 17β-hydroxysteroid dehydrogenase, said sequence being sufficiently homologous to SEQ ID No. 3 or a complement thereof, to hybridize under stringent conditions to SEQ ID No. 3, or its complement.

In a further embodiment, the invention provides a method for producing type 5 17β-hydroxysteroid dehydrogenase, comprising the steps of preparing a recombinant host transformed or transfected with the vector of the invention and culturing said host under conditions which are conducive to the production of type 5 17β-hydroxysteroid dehydrogenase by said host.

In an additional embodiment, the invention provides a method for determining the inhibitory effect of a test compound on the enzymatic activity of type 5 17β-hydroxysteroid dehydrogenase, comprising the steps of providing type 5 17β-hydroxysteroid dehydrogenase; contacting said type 5 17β-hydroxysteroid dehydrogenase with said test compound; and thereafter determining the enzymatic activity of said type 5 17β-hydroxysteroid dehydrogenase in the presence of said test compound.

In an additional embodiment, the invention provides a method of interfering with the expression of type 5 17β-hydroxysteroid dehydrogenase, comprising the step of administering nucleic acids substantially identical to at least 15 consecutive nucleotides of SEQ ID No. 1 or a complement thereof.

In a further embodiment, there is provided a method of interfering with the synthesis of type 5 17β-hydroxysteroid dehydrogenase, comprising the step of administering antisense RNA complementary to mRNA encoded by at least 15 consecutive nucleotides of SEQ ID No. 1 or a complement thereof.

In an additional embodiment, the invention provides a method of interfering with the expression of type 5 17β-hydroxysteroid dehydrogenase, comprising the step of administering nucleic acids substantially identical to at least 15 consecutive nucleotides of SEQ ID No. 3 or a complement thereof.

In another embodiment, the invention provides a method of interfering with the synthesis of type 5 17β-hydroxysteroid dehydrogenase, comprising the step of administering antisense RNA complementary to mRNA encoded by at least 15 consecutive nucleotides of SEQ ID No. 3 or a complement thereof.

In a further embodiment, there is provided a method for determining the inhibitory effect of antisense nucleic acids on the enzymatic activity of type 5 17β-hydroxysteroid dehydrogenase, comprising the steps of providing a host system capable of expressing type 5 17β-hydroxysteroid dehydrogenase; introducing said antisense nucleic acids into said host system; and thereafter determining the enzymatic activity of said type 5 17β-hydroxysteroid dehydrogenase.

Other features and advantages of the present invention will become apparent from the following description of the invention which refers to the accompanying drawings.

BRIEF DESCRIPTION OF THE DRAWINGS

FIG. 1A shows the substrate specificity of type 5 17β-HSD. The concentration of each substrate was 0.1 μM. FIG. 1B shows the time course amount of 20 -HSD and 17β-HSD activities of cells transfected with vectors containing human type 5 17β-HSD. The substrates, progesterone (P) and Δ⁴-dione, were added at a concentration of 0.1 μM;

FIGS. 3A, 3B and 3C is the cDNA sequence (SEQ ID No. 1) and the deduced amino acid sequence (SEQ ID No. 2) of human type 5 17β-HSD. The nucleotide sequence is numbered in the 5' to 3' direction with the adenosine of the initiation codon (ATG) designated as +11. The translation stop codon is indicated by asterisks. The potential post modification sites are underlined, wherein TSK=tyrosine sulfokinase; CK2=casein kinase II; PKC=protein kinase C; NG=N-glycosylation; and NM=N-myrystoylation;

FIGS. 5A-1, 5A-2, 5A-3, 5B-1, 5B-2, and 5B-3 are the nucleotide sequence of the chromosomal DNA of a gene which encodes type 5 17β-HSD. It includes SEQ ID Nos. 3 to 29.

DETAILED DESCRIPTION OF THE INVENTION

A gene encoding the enzyme, type 5 17β-HSD, has been isolated and encodes a protein having 323 amino acids with a calculated molecular weight of 36,844 daltons. As shown in FIGS. 3A, 3B and 3C, the coding portion of this gene includes nucleotides +11 through 982, including the stop codon (and encodes amino acids +1 through 323), numbered in the 5' to 3' direction.

Figure 4:
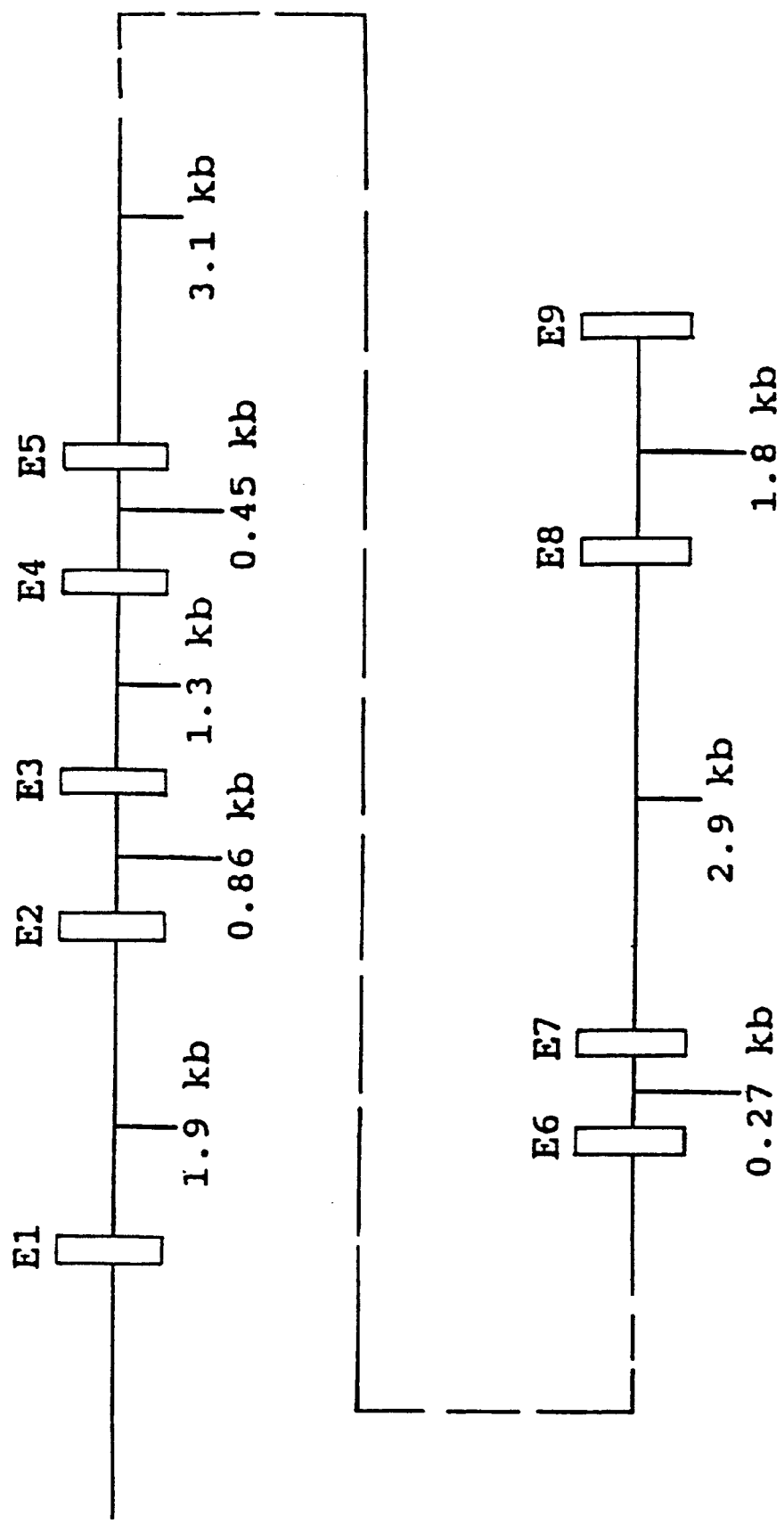
FIG. 4 is a map of the chromosomal DNA of a gene which encodes type 5 17β-HSD.

The chromosomal DNA fragment of the gene for type 5 17β-HSD has also been characterized. A map of the gene is provided in FIG. 4. In particular, it was found, using primer extension analysis, that the gene includes 16 kilobase pairs (kb) and contained nine short exons. A portion of the 5' flanking region, as set forth in SEQ ID No. 3, of the genomic DNA includes 730 base pairs (bp). Exon I (SEQ ID No. 4) contains 37 nucleotides in the 5' noncoding region and the nucleotides for the first 28 amino acids. The second intron region includes the nucleotides set forth in SEQ ID Nos. 5 and 6, which are 252 and 410 bp, respectively. These are joined by a 1.2 kb region which is not important and therefore, its sequence has been omitted. Exon 2 (SEQ ID No. 7) contains nucleotides for the following 56 amino acids of human type 5 17β-HSD. The following intron region includes SEQ ID Nos. 8 and 9, 700 and 73 bp, respectively, which are joined by a 0.1 kb region for which the sequence has not been provided. Exon 3 (SEQ ID No. 10) includes the next 117 nucleotides which specify the following 39 amino acids. The fourth intron region is represented by SEQ ID Nos. 11 and 12, 152 and 208 nucleotides in length, respectively, with a 0.9 kb region in between which has not been provided. Exon 4 (SEQ ID No. 13) includes the next 78 bp which specify the following 26 amino acids of the enzyme. Intron region five contains SEQ ID Nos. 14 and 15, with 98 and 249 nucleotides, respectively, with a 0.1 kb region in the middle which has not been provided. The fifth exon (SEQ ID No. 16) contains nucleotides for the following 41 amino acids of human type 5 17β-HSD. The sixth intron region, set forth in SEQ ID Nos. 17 and 18 with 138 and 189 bp, respectively, also includes a 2.8 kb region which has not been provided. Exon 6 (SEQ ID No. 19) contains nucleotides for the following 36 amino acids of type 5 17β-HSD, as well as two nucleotides of the codon 227 (Trp). The next intron region includes a 136 bp portion (SEQ ID No. 20) and a 66 bp portion (SEQ ID No. 21) which are joined by a 0.1 kb region which is not set forth. Exon 7 (SEQ ID No. 22) contains nucleotides for the third nucleotide of codon 227 (Trp) and nucleotides for the following 55 codons. The following intron region includes a 136 nucleotide region (SEQ ID No. 23), a 2.5 kb region which is not provided and a 286 bp region (SEQ ID No. 24). Exon 8 (SEQ ID No. 25) includes 83 nucleotides which code for the following 27 amino acids and 2 nucleotides of codon 310. The ninth intron region contains 713 nucleotides (SEQ ID No. 26) followed by a 1 kb region which has not been provided followed by a 415 nucleotide region (SEQ ID No. 27). Exon 9 (SEQ ID No. 28) contains the third nucleotide of codon 310, 42 nucleotides for the last 13 amino acids and a stop codon and approximately 200 nucleotides in the 3'-untranslated region. A polymorphic $(GT)_n$ repeat region that can be used to perform genetic linkage mapping of the type 5 17β-HSD can be found 255 nucleotides downstream from the TAA stop codon. SEQ ID No. 29 sets forth 109 bp of additional genomic sequence. The nucleotide sequence of the gene fragment, as described above, is provided in FIGS. 5A-1, 5A-2, 5A-3, 5B-1, 5B-2 and 5B-3.

The type 5 17β-HSD enzyme can be produced by incorporating the nucleotide sequence for the coding portion of the gene into a vector which is then transformed or transfected into a host system which is capable of expressing the enzyme. The DNA can be maintained transiently in the host or can be stably integrated into the genome of the host cell. In addition, the chromosomal DNA can be incorporated into a vector and transfected into a host system for cloning.

In particular, for the cloning and expression of type 5 17β-HSD, any common expression vectors, such as plasmids, can be used. These vectors can be prokaryotic expression vectors including those derived from bacteriophage λ such as λgt11 and λEMBL3, E. coli strains such as pBR322 and Bluescript (Stratagene); or eukaryotic vectors, such as those in the pCMV family. Vectors incorporating an isolated human cDNA shown in Sequence ID No. 1 (ATCC Deposit No. 97280) and the chromosomal DNA as shown in Sequence ID Nos. 3 through 29 (ATCC Deposit No. 97281) for type 5 17β-HSD have been placed on deposit at the American Type Culture Collection (ATCC, Rockville, Md.), in accordance with the terms of the Budapest Treaty, and will be made available to the public upon issuance of a patent based on the present patent application or as otherwise provided by the Budapest Treaty or applicable patent law.

These vectors generally include appropriate replication and control sequences which are compatible with the host system into which the vectors are transfected. A promoter sequence is generally included. For prokaryotes, some representative promoters include β-lactamase, lactose, and tryptophan. In mammalian cells, commonly used promoters include, but are not limited to, adenovirus, cytomegalovirus (CMV) and simian virus 40 (SV 40). The vector can also optionally include, as appropriate, an origin of replication, ribosome binding sites, RNA splice sites, polyadenylation sites, transcriptional termination sequences and/or a selectable marker. It is well understood that there are a variety of vector systems with various characteristics which can be used in the practice of the invention. A map of the pCMV vector, which is an example of a vector which can be used in the practice of the invention, is provided in FIG. 2.

Commonly known host systems which are known for expressing an enzyme, and which may be transfected with an appropriate vector which includes a gene for Type 5 17β-HSD can be used in the practice of the invention. These host systems include prokaryotic hosts, such as *E. coli,* bacilli, such as *Bacillus subtilus,* and other enterobacteria, such as Salmonella, Serratia, and Pseudomonas species. Eukaryotic microbes, including yeast cultures, can also be used. The most common of these is *Saccharomyces cerevisiae,* although other species are commercially available and can be used. Furthermore, cell cultures can be grown which are derived from mammalian cells. Some examples of suitable host cell lines include embryonal kidney (293), SW-13, chinese hamster ovary (CHO), HeLa, myeloma, Jurkat, COS-1, BHK, W138 and madin-darby canine kidney (MDCK). In the practice of the invention, the 293 cells are preferred.

Type 5 17β-HSD, whether recombinantly produced as described herein, purified from nature, or otherwise produced, can be used in assays to identify compounds which inhibit or alter the activity of the enzyme. In particular, since type 5 17β-HSD is shown to catalyze the conversion of progesterone to 20 -OH-P and the conversion of $\Delta^4$-dione to testosterone, this enzyme can be used to identify compounds which interfere with the production of these sex steroids. It is preferred that the enzyme be obtained directly from the recombinant host, wherein following expression, a crude homogenate is prepared which includes the enzyme. A substrate of the enzyme, such as progesterone or $\Delta^4$-dione and a compound to be tested are then mixed with the homogenate. The activity of the enzyme with and without the test compound is compared. Numerous methods are known which can be used to indicate the effects of the test compound on the activity of the substrate for easy detection of the relative amounts of substrate and product over time. For example, it is possible to label the substrate so that the label also stays on any product that is formed. Radioactive labels, such as $C^{14}$ or $H^3$, which can be quantitatively analyzed are particularly useful.

It is preferred that the mixture of the enzyme, test compound and substrate be allowed to incubate for a predetermined amount of time. In addition, it is preferred that the product is separated from the substrate for easier analysis. A number of separation techniques are known, for example, thin layer chromatography (TLC), high pressure liquid chromatography (HPLC), spectrophotometry, gas chromatography, mass spectrophotometry and nuclear magnetic resonance (NMR). However, any known method which can differentiate between a substrate and a product can be used.

It is also contemplated that the gene for type 5 17β-HSD or a portion thereof can be used to produce antisense nucleic acid sequences for inhibiting expression of Type 5 17β-HSD in vivo. Thus activity of the enzyme and levels of its products (e.g. testosterone) may be reduced where desirable. In general, antisense nucleic acid sequences can interfere with transcription, splicing or translation processes. Antisense sequences can prevent transcription by forming a triple helix or hybridizing to an opened loop which is created by RNA polymerase or hybridizing to nascent RNA. On the other hand, splicing can advantageously be interfered with if the antisense sequences bind at the intersection of an exon and an intron. Finally, translation can be affected by blocking the binding of initiation factors or by preventing the assembly of ribosomal subunits at the start codon or by blocking the ribosome from the coding portion of the mRNA, preferably by using RNA that is antisense to the message. For further general information, see Hélène et al., *Biochimica et Biophysica Acta,* 1049:99–125 (1990), which is herein incorporated by reference in its entirety.

An antisense nucleic acid sequence is an RNA or single stranded DNA sequence which is complementary to the target portion of the target gene. These antisense sequences are introduced into cells where the complementary strand base pairs with the target portion of the target gene, thereby blocking the transcription, splicing or translation of the gene and eliminating or reducing the production of type 5 17β-HSD. The length of the antisense nucleic acid sequence need be no more than is sufficient to interfere with the transcription, splicing or translation of functional type 5 17β-HSD. Antisense strands can range in size from 10 nucleotides to the complete gene, however, about 10 to 50 nucleotides are preferred, and 15 to 25 nucleotides are most preferred.

Although it is contemplated that any portion of the gene could be used to produce antisense sequences, it is preferred that the antisense is directed to the coding portion of the gene or to the sequence around the translation initiation site of the mRNA or to a portion of the promoter. Some examples of specific antisense oligonucleotide sequences in the coding region which can be used to block type 5 17β-HSD synthesis include: TTTAGCTTTACACACTGCTGTT (SEQ ID No. 30); TCCAAAGCTTTACTTCTCGG (SEQ ID No. 31); GATGAAAAGTGGACCA (SEQ ID No. 32); ATCTGTTG-GTGAAAGTTC (SEQ ID No. 33); TCCAGCTGCCT-GCGGT (SEQ ID No. 34); CTTGTACTTGAGTCCTG (SEQ ID No. 35); CTCCGGTTGAAATACGGA (SEQ ID No. 36); CATCGTTTGTCTCGTTGAGA (SEQ ID No. 37); TCACTGTTAAAATAGTGGAGAT (SEQ ID No. 38); ATCTGAATATGGATAAT (SEQ ID No. 39). Examples of antisense oligonucleotide sequences which can block the splicing of the type 5 17β-HSD premessage are as follows: TTCTCGGAACCTGGAGGAGC (SEQ ID No. 40); GACACAGTACCTTTGAAGTG (SEQ ID No. 41); TGGACCAAAGCTGCAGAGGT (SEQ ID No. 42); CCT-CACCTGGCTGAAATAGA (SEQ ID No. 43); AAGCACT-CACCTCCCAGGTG (SEQ ID No. 44); GACATTCTAC-CTGCAGTTGA (SEQ ID No. 45); CTCAAAAACCTATCAGAAA (SEQ ID No. 46); GGAAACTTACCTATCACTGT (SEQ ID No. 47); GCTAGCAAAACTGAAAAGAG (SEQ ID No. 48). Examples of antisense oligonucleotide sequences which inhibit the promoter activity of type 5 17β-HSd include: GAGAAATATTCATTCTG (SEQ ID No. 49); CGAGTC-CTGATAAAGCTG (SEQ ID No. 50); GATGAGGGTG-CAAATAA (SEQ ID No. 51); GGAGTGTTAATTAATAA-CAGTTT (SEQ ID No. 52); CAGAGATTACAAAAACAAT (SEQ ID No. 53); TGC-CTTTTTACATTTTCAATCA (SEQ ID No. 54); ACACAT-AATTTAAAGGA (SEQ ID No. 55); TTAAATTAT-TCAAAAGG (SEQ ID No. 56); AAGAGAAATATTCATTTCTG (SEQ ID No. 57); CCCCTCCCCCCACCCCTGCA (SEQ ID No. 58); CTGC-CGTGATAATGCCCC (SEQ ID No. 59).

As is well understood in the art, the oligonucleotide sequences can be modified in various manners in order to increase the effectiveness of the treatment with oligonucleotides. In particular, the sequences can be modified to include additional RNA to the 3' end of the RNA which can form a hairpin-loop structure and thereby prevent degradation by nucleases. In addition, the chemical linkages in the backbone of the oligonucleotides can be modified to also prevent cleavage by nucleases.

There are numerous methods which are known in the art for introducing the antisense strands into cells. One strategy is to incorporate the gene which encodes type 5 17β-HSD in the opposite orientation in a vector so that the RNA which is transcribed from the plasmid is complementary to the mRNA transcribed from the cellular gene. A strong promoter, such as pCMV, is generally included in the vector, upstream of the gene sequence, so that a large amount of the antisense RNA is produced and is available for binding sense mRNA. The vectors are then transfected into cells which are then administered. It is also possible to produce single stranded DNA oligonucleotides or antisense RNA and incorporate these into cells or liposomes which are then administered. The use of liposomes, such as those described in WO95/03788, which is herein incorporated by reference, is preferred. However, other methods which are well understood in the art can also be used to introduce the antisense strands into cells and to administer to these patients in need of such treatment.

The following is an example of the expression of human type 5 17β-HSD. This example is intended to be illustrative of the invention and it is well understood by those of skill in the art that modifications, alterations and different techniques can be used within the scope of the invention.

Figure 2:
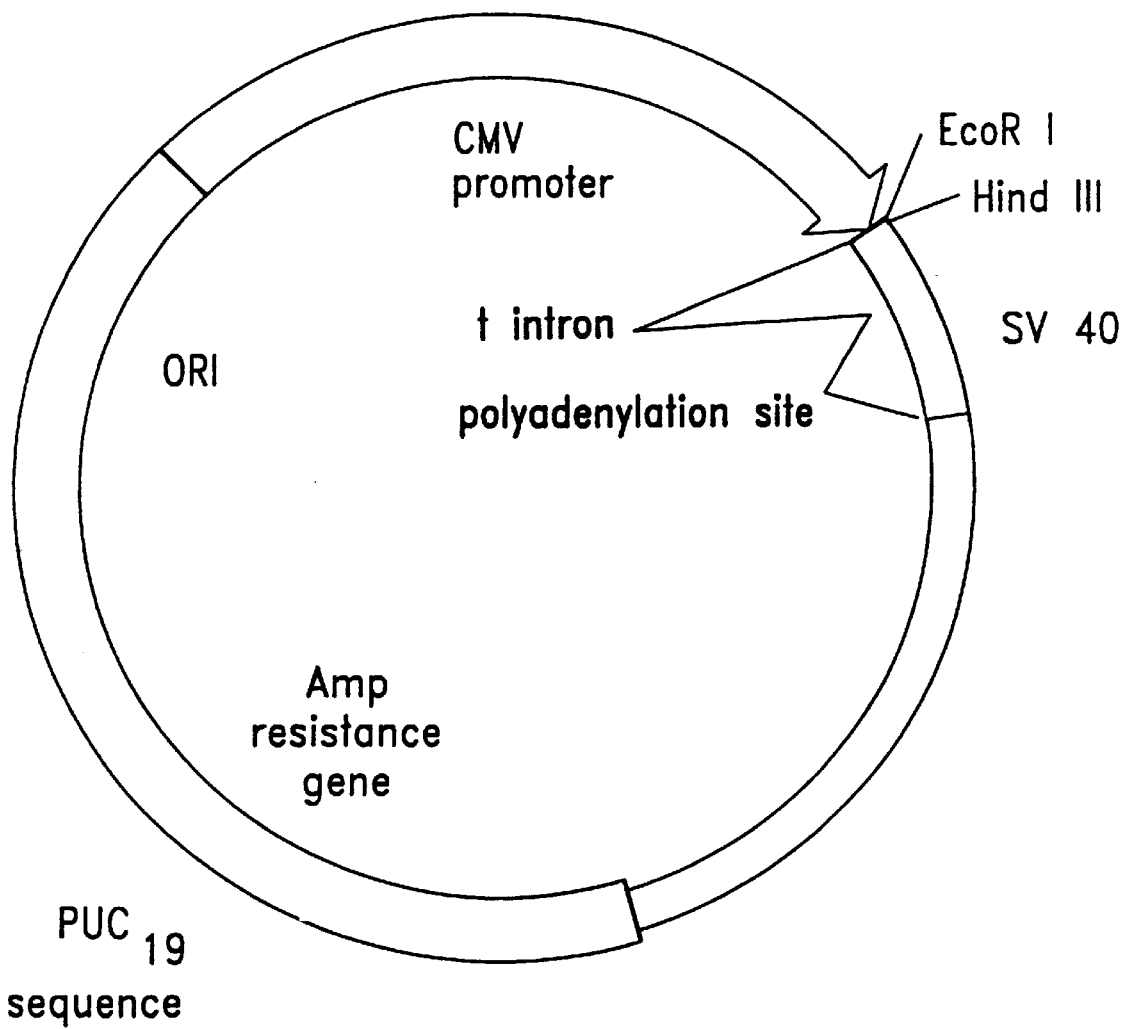
FIG. 2 is a map of a pCMV vector which is exemplary of one that can be used to transfect host cells in accordance with the invention.

Expression of 20, 17β-HSD (Type 5 17β-HSD)
Construction of the expression vector and nucleotide sequence determination The phage DNA were digested with EcoRI restriction enzyme and the resulting cDNA fragments were inserted in the EcoRI site downstream to the cytomegalovirus (CMV) promoter of the pCMV vector as shown in FIG. 2. The recombinant pCMV plasmids were amplified in *Escherichia coli* DH5α competent cells, and were isolated using the alkaline lysis procedure as described by Maniatis in Molecular Cloning: A Laboratory Manual (Cold Spring Harbor Press 1982). The sequencing of double-stranded plasmid DNA was performed according to the dideoxy chain termination method described by Sanger F. et al., *Proc. Natl. Acad. Sci.*, 74:5463–5467 (1977) using a T7 DNA polymerase sequencing kit (Pharmacia LKB Biotechnology). In order to avoid errors, all sequences were determined by sequencing both strands of the DNA. The oligonucleotide primers were synthesized using a 394 DNA/RNA synthesizer (Applied Biosystem).

As shown in FIG. 2, the pCMV vector contains 582 nucleotides of the pCMV promoter, followed by 74 nucleotides of unknown origin which includes the EcoRI and HindIII sites, followed by 432 basepairs (bp) of a small t intron (fragment 4713–4570) and a polyadenylation signal (fragment 2825–2536) of SV40, followed by 156 nucleotides of unknown origin, followed by 1989 bp of the PvuII (628) to AatII (2617) fragment from the pUC 19 vector (New England Biolabs) which contains an *E. coli* origin of replication and an ampicillin resistance gene for propagation in *E. coli*.

Transient expression in transformed embryonal kidney (293) cells

The vectors were transfected using the calcium phosphate procedure described by Kingston, R. E., In: Current Protocols in Molecular Biology, Ausubel et al. eds., pp. 9.1.1–9.1.9, John Wiley & Sons, N.Y. (1987) and used 1 to 10 μg of recombinant plasmid DNA per $10^6$ cells. The total amount of DNA is kept at 10 μg of plasmid DNA per $10^6$ cells by completing with pCMV plasmid without insert. The cells were initially plated at $10^4$ cells/cm$^2$ in Falcon® culture flasks and grown in Dulbecco's modified Eagle's medium containing 10% (vol/vol) fetal bovine serum (hyclone, Logan, Utah) under a humidified atmosphere of air/$CO^2$ (95%/5%) at 37° C. and supplemented with 2 mM L-glutamine, 1 mM sodium pyruvate, 100 IU penicillin/ml, and 100 μbg streptomycin sulfate/ml.

Assay of enzymatic activity

The determination of enzymatic activity was performed as described by Luu-The et al., *Biochemistry*, 13:8861–8865 (1991) which is herein incorporated by reference. See also Lachance et al., *J. Biol. Chem.*, 265:20469–20475 (1990). Briefly, 0.1 μM of the indicated $^{14}$C-labeled substrate (Dupont Inc. (Canada)), namely, dehydroepiandrosterone (DHEA), 4-androstene-3,17-dione ($\Delta^4$-dione), testosterone (T), estrone (E1), estradiol (E2), dihydrotestosterone (DHT), and progesterone (PROG), was added to freshly changed culture medium in a 6-well culture plate. After incubation for 1 hour, the steroids were extracted twice with 2 ml of ether. The organic phase was pooled and evaporated to dryness. The steroids were solubilized in 50 μl of dichloromethane, applied to a Silica gel 60 thin layer chromatography (TLC) plate (Merck, Darmstad, Germany) and then separated by migration in the toluene-acetone (4:1) solvent system (Luu-The, V. et al., *J. Invest. Dennatol.*, 102:221–226 (1994) which is herein incorporated by reference). The substrates and metabolites were identified by comparison with reference steroids, revealed by autoradiography and quantitated using the Phosphoimager System (Molecular Dynamics, Sunnyvale, Calif.).

Cloning of the type 5 17β-HSD genomic DNA clone

The hybridization and sequencing methods were as described above and as previously described (Luu-The et al., *Mol. Endocrinol.*, 4:268–275 (1990); Luu-The et al., *DNA and Cell Biol.*, 14:511–518 (1995); Lachance et al., *J. Biol. Chem.*, 265:20469–20475 (1990); Lachance et al., *DNA and Cell Biol.* 10:701–711 (1991); Bernier et al., *J. Biol. Chem,* 269, 28200–28205, (1994) which are herein incorporated by reference).

About 20 recombinant clones which gave the strongest hybridization signal were selected for second and third screening in order to isolate a single phage plaque. The two longest clones that hybridized with specific oligonucleotides probes located at the 5' and 3' regions of type 5 17β-HSD, respectively, were selected for mapping, subcloning and sequencing. As shown in FIGS. 4 and 5A-1, 5A-2, 5A-3, 5B-1, 5B-2 and 5B-3, the gene is included in approximately 16 kilobase pairs of introns and contains 9 short exons. A primer extension analysis using oligoprimer CAT-CAT-TTA-GCT-TTA-CAT-ACT-GCT-G, (complement of nucleotides 47 to 23 of SEQ. ID. NO: 1) located at positions 13 to 27, indicates that the start site is situated 37 nucleotides upstream from the ATG initiating codon.

The sites and signatures in the primary protein sequence were detected using PC/Gene software (Intelli Genetics Inc., Mountain View, Calif.). This analysis revealed a potential N-glycosylation site at Asn-198; five protein kinase C sites at Ser-73, Thr-82, Ser-102, Ser-121, and Ser-221; five casein kinase II phosphorylation sites at Ser-129, Thr-146, Ser-221, Ser-271, and Thr-289; two N-myristoylation sites at Gly-158 and Gly-298; a tyrosine sulfatation site at Tyr-55; an aldo/keto reductase family signature 1 (25) at amino acids 158 to 168 and an aldo/keto reductase family putative active site signature at amino acids 262 to 280.

Figure 1A:
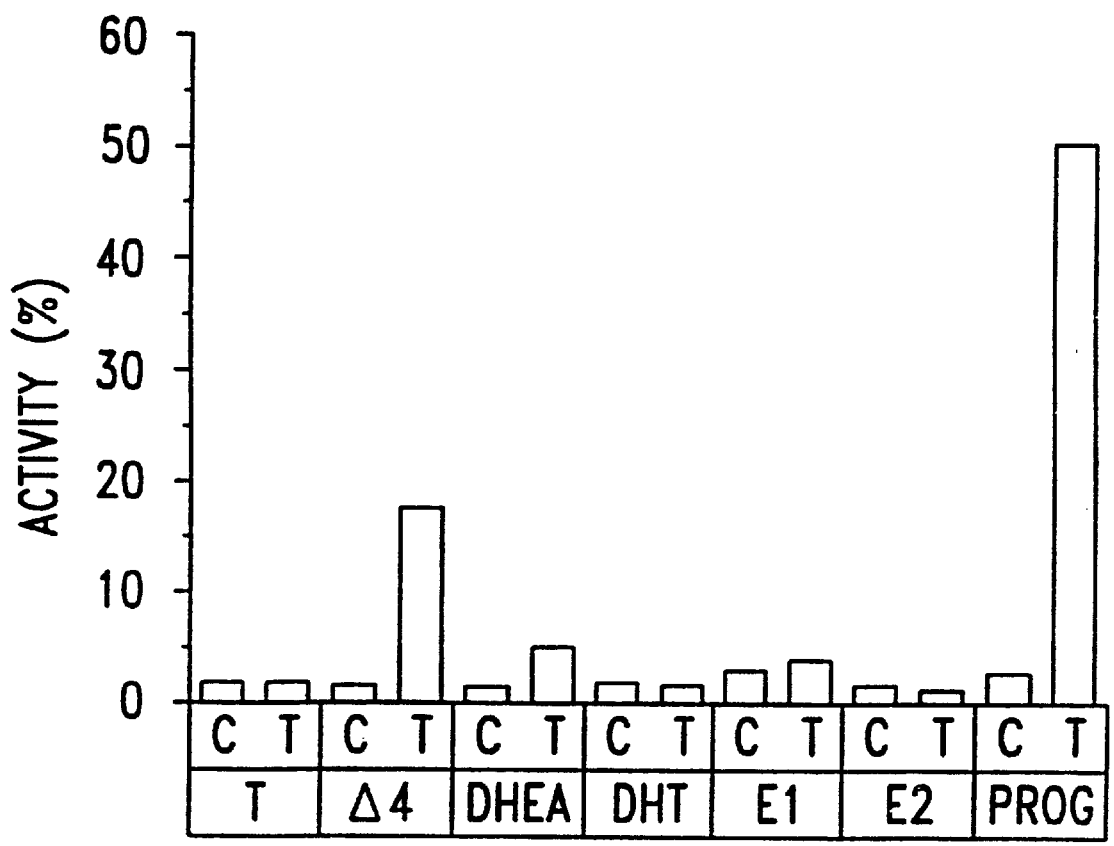
FIGS. 1A and 1B are graphs showing the enzymatic activities of Type 5 17β-HSD on various substrates. The enzyme was expressed in embryonal kidney (293) cells (ATCC CRL 1573) which were transfected with a vector, prepared in accordance with the invention, and containing the gene encoding human type 5 17β-HSD
Figure 1B:
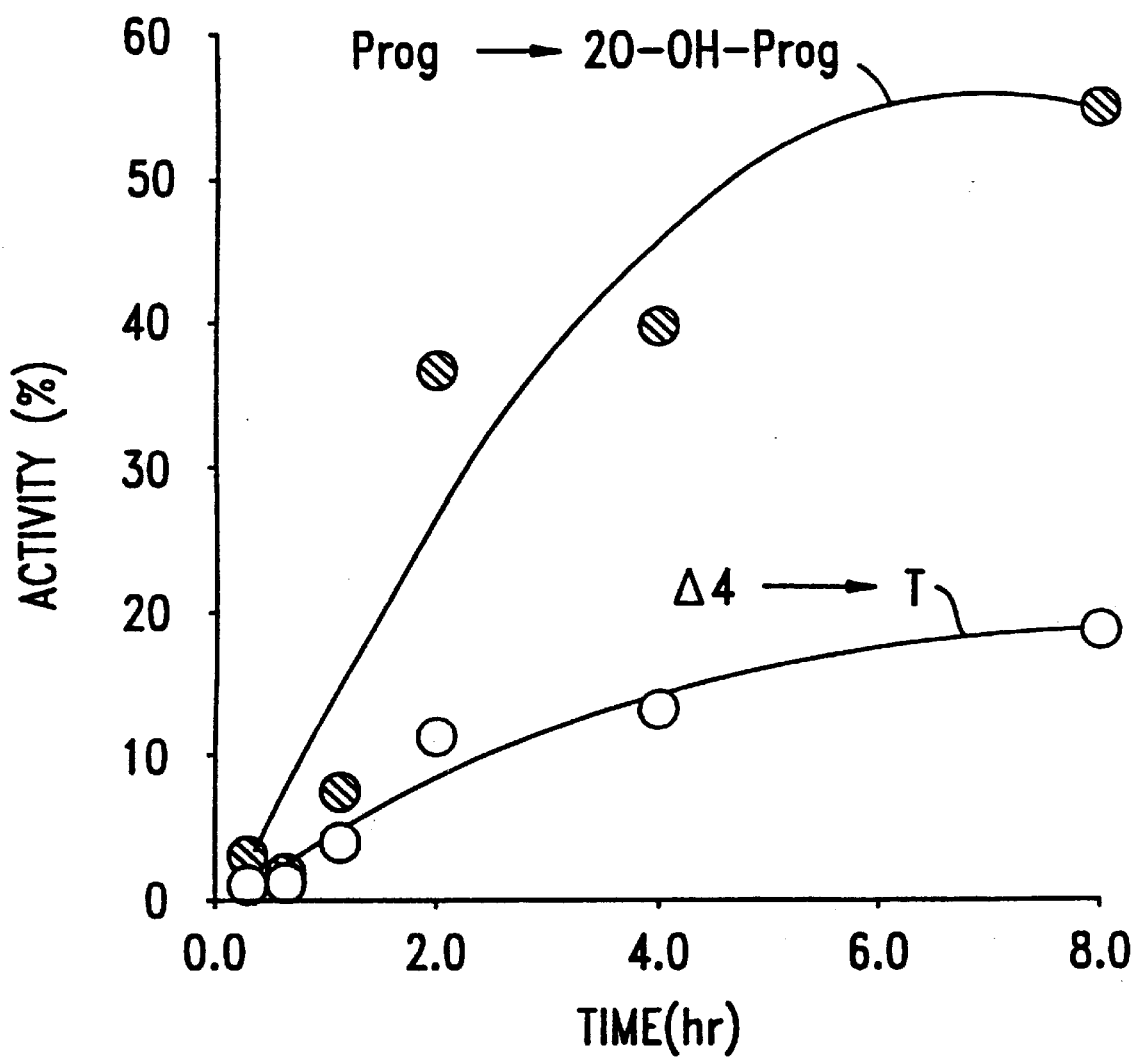

As described above, the enzymatic activity of the type 5 17β-HSD was evaluated by transfecting 293 cells with vectors which included the gene encoding human type 5 17β-HSD. The ability of the enzyme to catalyze the transformation of progesterone (P) to 20 -hydroxyprogesterone (20 -OH-P), 4-androstenedione ($\Delta^4$-dione) to testosterone (T), 5 -androstane-3,17-dione (A-dione) to dihydrotestosterone (DHT), dehydroepiandrosterone (DHEA) to 5-androstene-3β,17β-diol, and estrone (E1) to estradiol (E2) was analyzed. As shown in FIG. 1A, the enzyme possesses high reductive 20-HSD activity, wherein progesterone (P) is transformed to the inactive 20-OH-P, and 17β-HSD activity, wherein Δ⁴dione is converted to testosterone (T). However, 3-HSD activity which is responsible for the transformation of DHT to 5α-androstane-3α,17β-diol is negligible. The ability of this enzyme to transform E1 and E2 was also negligible (FIG. 1A). FIG. 1B shows that the 20-HSD and 17β-HSD activities increased over time.

The isolated amino acid sequence of human type 5 17β-HSD was also compared with rabbit 20-HSD (rb), rat 20-HSD (r), human 3-HSD (h), rat 3-HSD (r), bovine prostaglandin f synthase (b pgfs), frog ρ-crystallin (f ρ-crys) and human type 1 and type 217β-HSDs (h). These sequences show 76.2%, 70.7%, 84.0%, 68.7%, 78.3%, 59.7%, 15.2% and 15.0% identity with type 5 17β-HSD, respectively.

Although the present invention has been described in relation to particular embodiments thereof, many other variations and modifications and other uses will be apparent to those skilled in the art.

We claim:

1. An isolated nucleotide sequence encoding type 5 17β-hydroxysteroid dehydrogenase, said sequence including the exact sequence of SEQ ID No. 1, or nucleotides 11–981 thereof, or a complement of either of the foregoing, said sequence encoding an enzyme which catalyzes the conversion of progesterone to 20α-hydroxyprogesterone and the conversion of 4-androstenedione to testosterone.

2. The nucleotide sequence, as recited in claim 1, wherein said sequence includes the region from nucleotides 11–981 of SEQ ID No. 1.

3. A recombinant expression vector comprising a promoter sequence operably linked to a nucleotide sequence in accordance with claim 1.

4. A recombinant expression vector comprising a promoter sequence operably linked to a nucleotide sequence in accordance with claim 2.

5. A recombinant host cell, transformed or transfected with the vector of claim 4.

6. The recombinant host cell of claim 5, wherein said host cell is a eukaryotic cell.

7. A recombinant host cell, transformed or transfected with the vector of claim 3.

8. The recombinant host cell of claim 7, wherein said host cell is a eukaryotic cell.

9. A recombinant host cell including the exact nucleotide sequence of SEQ ID No. 1 or its complement integrated into the genome of said host cell.

10. The recombinant host cell of claim 9, wherein said nucleotide sequence is located on a recombinant vector.

11. The recombinant host cell, as recited in claim 8, wherein said host cell expresses a biologically active type 5 17β-hydroxysteroid dehydrogenase.

12. A method for producing type 5 17β-hydroxysteroid dehydrogenase, comprising the steps of:

preparing a recombinant host transformed or transfected with the vector of claim 3; and culturing said host under conditions which are conducive to the production of type 5 17β-hydroxysteroid dehydrogenase by said host.

* * * * *

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
        (A) LENGTH: 1206 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 11..982

(xi) SEQUENCE DESCRIPTION: SEQ ID NO:1:

```
GTGACAGGGA ATG GAT TCC AAA CAG CAG TGT GTA AAG CTA AAT GAT GGC         49
           Met Asp Ser Lys Gln Gln Cys Val Lys Leu Asn Asp Gly
             1               5                  10

CAC TTC ATG CCT GTA TTG GGA TTT GGC ACC TAT GCA CCT CCA GAG GTT        97
His Phe Met Pro Val Leu Gly Phe Gly Thr Tyr Ala Pro Pro Glu Val
         15                  20                  25

CCG AGA AGT AAA GCT TTG GAG GTC ACC AAA TTA GCA ATA GAA GCT GGG       145
Pro Arg Ser Lys Ala Leu Glu Val Thr Lys Leu Ala Ile Glu Ala Gly
 30                  35                  40                  45

TTC CGC CAT ATA GAT TCT GCT CAT TTA TAC AAT AAT GAG GAG CAG GTT       193
Phe Arg His Ile Asp Ser Ala His Leu Tyr Asn Asn Glu Glu Gln Val
                 50                  55                  60

GGA CTG GCC ATC CGA AGC AAG ATT GCA GAT GGC AGT GTG AAG AGA GAA       241
Gly Leu Ala Ile Arg Ser Lys Ile Ala Asp Gly Ser Val Lys Arg Glu
                     65                  70                  75

GAC ATA TTC TAC ACT TCA AAG CTT TGG TCC ACT TTT CAT CGA CCA GAG       289
Asp Ile Phe Tyr Thr Ser Lys Leu Trp Ser Thr Phe His Arg Pro Glu
                 80                  85                  90

TTG GTC CGA CCA GCC TTG GAA AAC TCA CTG AAA AAA GCT CAA TTG GAC       337
Leu Val Arg Pro Ala Leu Glu Asn Ser Leu Lys Lys Ala Gln Leu Asp
             95                  100                 105

TAT GTT GAC CTC TAT CTT ATT CAT TCT CCA ATG TCT CTA AAG CCA GGT       385
Tyr Val Asp Leu Tyr Leu Ile His Ser Pro Met Ser Leu Lys Pro Gly
110                 115                 120                 125

GAG GAA CTT TCA CCA ACA GAT GAA AAT GGA AAA GTA ATA TTT GAC ATA       433
Glu Glu Leu Ser Pro Thr Asp Glu Asn Gly Lys Val Ile Phe Asp Ile
                 130                 135                 140

GTG GAT CTC TGT ACC ACC TGG GAG GCC ATG GAG AAG TGT AAG GAT GCA       481
Val Asp Leu Cys Thr Thr Trp Glu Ala Met Glu Lys Cys Lys Asp Ala
             145                 150                 155

GGA TTG GCC AAG TCC ATT GGG GTG TCA AAC TTC AAC CGC AGG CAG CTG       529
Gly Leu Ala Lys Ser Ile Gly Val Ser Asn Phe Asn Arg Arg Gln Leu
         160                 165                 170
```

```
GAG ATG ATC CTC AAC AAG CCA GGA CTC AAG TAC AAG CCT GTC TGC AAC        577
Glu Met Ile Leu Asn Lys Pro Gly Leu Lys Tyr Lys Pro Val Cys Asn
    175                 180                 185

CAG GTA GAA TGT CAT CCG TAT TTC AAC CGG AGT AAA TTG CTA GAT TTC        625
Gln Val Glu Cys His Pro Tyr Phe Asn Arg Ser Lys Leu Leu Asp Phe
190                 195                 200                 205

TGC AAG TCG AAA GAT ATT GTT CTG GTT GCC TAT AGT GCT CTG GGA TCT        673
Cys Lys Ser Lys Asp Ile Val Leu Val Ala Tyr Ser Ala Leu Gly Ser
                210                 215                 220

CAA CGA GAC AAA CGA TGG GTG GAC CCG AAC TCC CCG GTG CTC TTG GAG        721
Gln Arg Asp Lys Arg Trp Val Asp Pro Asn Ser Pro Val Leu Leu Glu
                225                 230                 235

GAC CCA GTC CTT TGT GCC TTG GCA AAA AAG CAC AAG CGA ACC CCA GCC        769
Asp Pro Val Leu Cys Ala Leu Ala Lys Lys His Lys Arg Thr Pro Ala
                240                 245                 250

CTG ATT GCC CTG CGC TAC CAG CTG CAG CGT GGG GTT GTG GTC CTG GCC        817
Leu Ile Ala Leu Arg Tyr Gln Leu Gln Arg Gly Val Val Val Leu Ala
                255                 260                 265

AAG AGC TAC AAT GAG CAG CGC ATC AGA CAG AAC GTG CAG GTT TTT GAG        865
Lys Ser Tyr Asn Glu Gln Arg Ile Arg Gln Asn Val Gln Val Phe Glu
270                 275                 280                 285

TTC CAG TTG ACT GCA GAG GAC ATG AAA GCC ATA GAT GGC CTA GAC AGA        913
Phe Gln Leu Thr Ala Glu Asp Met Lys Ala Ile Asp Gly Leu Asp Arg
                290                 295                 300

AAT CTC CAC TAT TTT AAC AGT GAT AGT TTT GCT AGC CAC CCT AAT TAT        961
Asn Leu His Tyr Phe Asn Ser Asp Ser Phe Ala Ser His Pro Asn Tyr
                305                 310                 315

CCA TAT TCA GAT GAA TAT TAA CATGGAGACT TTGCCTGATG ATGTCTACCA          1012
Pro Tyr Ser Asp Glu Tyr  *
            320

GAAGGCCCTG TGTGTGGATG GTGACGCAGA GGACGTCTCT ATGCCGGTGA CTGGACATAT    1072

CACCTCTACT TAAATCCGTC CTGTTTAGCG ACTTCAGTCA ACTACAGCTC ACTCCATAGG    1132

CCAGAAATAC AATAAATCCT GTTTAGCGAC TTCAGTCAAC TACAGCTCAC TCCATAGGCC    1192

AGAAATACAA TAAA                                                      1206

(2) INFORMATION FOR SEQ ID NO:2:

(i) SEQUENCE CHARACTERISTICS:
        (A) LENGTH:  323 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Ser Lys Gln Gln Cys Val Lys Leu Asn Asp Gly His Phe Met
 1               5                  10                  15

Pro Val Leu Gly Phe Gly Thr Tyr Ala Pro Glu Val Pro Arg Ser
            20                  25                  30

Lys Ala Leu Glu Val Thr Lys Leu Ala Ile Glu Ala Gly Phe Arg His
            35                  40                  45

Ile Asp Ser Ala His Leu Tyr Asn Asn Glu Glu Gln Val Gly Leu Ala
        50                  55                  60

Ile Arg Ser Lys Ile Ala Asp Gly Ser Val Lys Arg Glu Asp Ile Phe
65                  70                  75                  80

Tyr Thr Ser Lys Leu Trp Ser Thr Phe His Arg Pro Glu Leu Val Arg
            85                  90                  95
```

```
Pro Ala Leu Glu Asn Ser Leu Lys Lys Ala Gln Leu Asp Tyr Val Asp
             100                 105                 110

Leu Tyr Leu Ile His Ser Pro Met Ser Leu Lys Pro Gly Glu Glu Leu
        115                 120                 125

Ser Pro Thr Asp Glu Asn Gly Lys Val Ile Phe Asp Ile Val Asp Leu
    130                 135                 140

Cys Thr Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Arg Ser Lys Leu Leu Asp Phe Cys Lys Ser
        195                 200                 205

Lys Asp Ile Val Leu Val Ala Tyr Ser Ala Leu Gly Ser Gln Arg Asp
    210                 215                 220

Lys Arg Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Val Leu Ala Lys Ser Tyr
            260                 265                 270

Asn Glu Gln Arg Ile Arg Gln Asn Val Gln Val Phe Glu Phe Gln Leu
        275                 280                 285

Thr Ala Glu Asp Met Lys Ala Ile Asp Gly Leu Asp Arg Asn Leu His
    290                 295                 300

Tyr Phe Asn Ser Asp Ser Phe Ala Ser His Pro Asn Tyr Pro Tyr Ser
305                 310                 315                 320

Asp Glu Tyr (2) INFORMATION FOR SEQ ID NO:3:

(i) SEQUENCE CHARACTERISTICS:
        (A) LENGTH: 730 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

AAGAACAAAT ACTATTAAGG CACTGCTTGC ATATATTAAA TGATGTCCAA ACTCCAAAAA      60

CTGTTAATAA TTAACACTCC AATAAAAACT ACACCAGAAT TCTTTTTAT TTGCACCCTC     120

ATCAGGATTA CAGCTTTATC AGGACTGCAT CTTCTTCAGA AATGAATATT TCTCTTACAA    180

CGCAAAGAAA GAAAAATCAA AATAAATTTT CTGATTGAAA ATGTAAAAAG GCAAATATTT    240

TTACAGTTTT AACTTTAATT TTTTATTGAG GACCAACTGT TTGAAAAATT CTCATTAGTC    300

ATTCCTTTAA ATTATGTGTA TGTGAGAGAA AGACGTAAGA TGGTTAATTA TTTCAAATGA    360

TGCAGTATAA AGAAGGGGCA TTATCACGGC AGAAACGAAA AAAGATATTT GTAGCTGGAG    420

GTTTTTATAG TCTAACATAT GGTTGCTATT TGTTCTACAA ATCCTTTTGA ATAATTTAAT    480

ATAGAGATTT CGAATAGAAA ATAATACTTT AGATAGAAAT TAATGAGTTT ATTATAACCA    540
```

```
TATATTATAA TAATTTACTT AGGAATTCTC TTTGATAAGA AACAAATGAA CTGAATGCAA      600

TTTTCTCCAC AGACCATATA AGACTGCCTA TGTACCTCCT CCTACATGCC ATTGGTTAAC      660

CATCAGTCAG TTTGCAGGGG TGGGGGGAGG GGTTTCCTGC CCATTGTTTT TGTAATCTCT      720

GAGGAGAAGC                                                             730
```

(2) INFORMATION FOR SEQ ID NO:4:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 38..121

(xi) SEQUENCE DESCRIPTION: SEQ ID NO:4:

```
AGCAGCAAAC ATTTGCTAGT CAGACAAGTG ACAGGGAATG GATTCCAAAC AGCAGTGTGT       60

AAAGCTAAAT GATGGCCACT TCATGCCTGT ATTGGGATTT GGCACCTATG CACCTCCAGA      120

G                                                                     121
```

(2) INFORMATION FOR SEQ ID NO:5:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

```
GTAAGAATAA TTCCTTTTAG TTTTCGGATT TCAAAAGAAT AAACCTAGTA GAAGTGAAAC       60

CCGTATTGGG TTGTAAGGTT CGTGTTCCTA CCTTACTCTG GATGACTCAC TGGTCTAGGT      120

TTCCTAGGCT AGGAGAAAAA AGTAGGCAAT CCTTGTTCTG CATTGAGGTC CATTCCTATG      180

GTCACGTACT GCTTATTTTT CGTTTGTGCA CTGTTTCTTT CTTCTGTTCA TGTCTAGTTC      240

CCAGCTTGGC AG                                                         252
```

(2) INFORMATION FOR SEQ ID NO:6:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

```
GGAAGTCTGA GTGAGCATTC TGTGTAATAT CACTGGGAGA GAACTCATAT GAGCTTGCAC      60

CGTTTCCCTT CTATACTCCA TGTGATTTTT ACCATGTATA ATATCACTAT ATTAAAAATA     120

ATTAGGACTA TTTCAGTCAT GTTAACTTTT CCAACAAATC ACTGAATCTG AGGGTGTTAT     180

GTGGTACCTC CATAACAGTG ATCAACCAGA GATTGCCTGA GACTGAAGGT GTTTCTGGGA     240

TGCTCAACCT TTATTACTAA CCAGGAAAGA CTCAGGCAAA CTGAGATGGA CTTTTCACCC     300

CACATACAGA CAGGAGGAAA AGCTGATTCT TGTATAAAAG TCAATGCTTG TGCCTGAACT     360

ACCTCTCAGC CACAGTGATC ACCAGATACT ACCTTTGGTT GCTCCTCCAG                410
```

(2) INFORMATION FOR SEQ ID NO:7:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 1..168

(xi) SEQUENCE DESCRIPTION: SEQ ID NO:7:

```
GTTCCGAGAA GTAAAGCTTT GGAGGTCACA AAATTAGCAA TAGAAGCTGG GTTCCGCCAT      60

ATAGATTCTG CTCATTTATA CAATAATGAG GAGCAGGTTG GACTGGCCAT CCGAAGCAAG     120

ATTGCAGATG GCAGTGTGAA GAGAGAAGAC ATATTCTACA CTTCAAAG                  168
```

(2) INFORMATION FOR SEQ ID NO:8:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

```
GTACTGTGTC TATGATGAGC TTGTGTGCAC ATGTATTTAT TGTGATTGTG TGGAGATGAC      60

AATTCTATGA CTGGATGAGT AGTTGTGGGT GAATTTGCT TCTGGGTTCA AATTTATTCA      120

CACATACTCA CATACTAAAA CTGAAATCAA ATCAAGGAA TGATGATCAC TTTTCATTTT      180

GGCTGTGTTC CAATTTATGA CCTGAAAGTC CCTTTACTTT TTTGAGCTTC AGCCGAGATC     240

AGTGTGATTT GACATGTGCT ATAGAATCAC AGAGAACAAT AATCATGTTA TGGTTTTTCT     300

TATCGCCTGG GTGATTTTCT AAGATTTCTT ATTATTCTCT CAATTGCTAT CTTTATCAGT     360

GAGATAGAAA GCAATATAAG AAAGCTCTGG GAGTATTAAA TAATAGACAC TTAAATTGTC     420

CTAAATTGTG TCCAGCATAG TGAGCATGTT CAAAACTTGT TTTACCCCCC TTTTATGTTG     480

CTTTAGTTTC TAAGCAACAT AAATAGCTAT TCTTAAGCAT TGGGTTGAAT GGATAGAAGA     540

ATTAGACTGT TAAAATGAGT TGTAAACTCT ACTGAAGATA ATTCAGGTAA CATCATAGTT     600

ATTACTTAAT ACTAATCTTT ACATTTTAAG AATTTACTCC TATCATTCAG TAGATGTACA     660
```

```
AACTATACAT CCAACGTATA ATAAAGTTTA TAAGGATAGG                             700
```

(2) INFORMATION FOR SEQ ID NO:9:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
ACTAGATGGC ACAAAGTAAT AAGATTTGCT CAAGCATTCA TTCAAAATCA CCTCCATTCT        60

TTAACCTCTG CAG                                                          73
```

(2) INFORMATION FOR SEQ ID NO:10:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 1..117

(xi) SEQUENCE DESCRIPTION: SEQ ID NO:10:

```
CTTTGGTCCA CTTTTCATCG ACCAGAGTTG GTCCGACCAG CCTTGGAAAA CTCACTGAAA        60

AAAGCTCAAT TGGACTATGT TGACCTCTAT CTTATTCATT CTCCAATGTC TCTAAAG          117
```

(2) INFORMATION FOR SEQ ID NO:11:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

```
GTATGCAGTT TGTATGAGCA TAAAATTGCG CTTCTGCTGT CATTATAAAC ATTGTTTATC        60

TGGATAGTTG AACAGAGCTT TTTATTAGGA GGATGTAGGG ATTATCACAC AGAAGAAGAA       120

CCGTAAGTGG AACACCTAAT TTCCTTTCTT TC                                    152
```

(2) INFORMATION FOR SEQ ID NO:12:

(i) SEQUENCE CHARACTERISTICS:
        (A) LENGTH: 208 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

```
ATATAATATT TGTAAGAGAT TAGAGGAAGC CTGTCTCCTG AATACATTCC TTATACCTTC      60

ATATGTAAAA CACTTAGCAC ATATCACTTT CTGGAGCATT GTACCACCTG TCTCATGGAG     120

GATTAGTGTC CTTAAAGGTA CCTGGGGTTA CAGCTATGAG TGGAGAAATT AATTTGTGAC     180

ATCATTAAAA TGACTGCTTC TATTTCAG                                        208
```

(2) INFORMATION FOR SEQ ID NO:13:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 1..78

(xi) SEQUENCE DESCRIPTION: SEQ ID NO:13:

```
CCAGGTGAGG AACTTTCACC AACAGATGAA AATGGAAAAG TAATATTTGA CATAGTGGAT      60

CTCTGTACCA CCTGGGAG                                                    78
```

(2) INFORMATION FOR SEQ ID NO:14:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

```
GTGAGTGCTT GGCGGAGAGG ACACAGAGAA GGATGACAAA AAGAGAAAAT CTGTTTCCCA      60

GGTTCGATAG GAAAGAATGG AATATGCACC ATTAGATC                              98
```

(2) INFORMATION FOR SEQ ID NO:15:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

GACAGGAATC TCTTTCCTTG CTTGTGCATT AATCTATGCA GTTTCCTAAG GAAGAGATAG      60

AAATTCTTAC TCTTGCTGCC TCTATCTTCT TCCCCTATTT GCTGTTTGAA TTTTTCTTTT     120

TTTGACAATC ACTGCTAGCT ATTTTCATTG TCATACTTTG AAAGTTGTTG CTCTCACAGT     180

TCTGTCTTGC ATTTACCGTG ATTTGCAGCC AACTGCACAA ATAATTCCTC ACAACCCCTT     240

TCTCCACAG                                                            249

(2) INFORMATION FOR SEQ ID NO:16:

(i) SEQUENCE CHARACTERISTICS:
        (A) LENGTH: 123 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 1..123

(xi) SEQUENCE DESCRIPTION: SEQ ID NO:16:

GCCATGGAGA AGTGTAAGGA TGCAGGATTG GCCAAGTCCA TTGGGGTGTC AAACTTCAAC      60

CGCAGGCAGC TGGAGATGAT CCTCAACAAG CCAGGACTCA AGTACAAGCC TGTCTGCAAC     120

CAG                                                                  123

(2) INFORMATION FOR SEQ ID NO:17:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

GTGAGCTCCC TTGGCCTTCT CTCCTTTCGG TTCTTCATGC CCCCTCTTCC TGTCCTATTG      60

CCAAATATCT GTTTGTTTTG TCCCAGTTAT CTTTGTGAAG TAGAAGATTA TCTAGAGAGC     120

AAAGCTTCTG TCAAGAAA                                                  138

(2) INFORMATION FOR SEQ ID NO:18:

(i) SEQUENCE CHARACTERISTICS:
        (A) LENGTH: 189 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

```
ATTTCCATTT ATACTTTTAG AAGATATATA AAATTTATTT CTATGAAAAA GGTTATTACT      60

TGACAATAAT ATCCTCAGCT CAAATATAAT GCTATACTGA TTATTATTCA GCTTCCTTAC     120

TTTCATCTTT TCAATATTAA CATAACTATT TCATATAAAT TGATGCTTCT CTCTTTTGGT     180

CAACTGCAG                                                             189
```

(2) INFORMATION FOR SEQ ID NO:19:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 1..110

(xi) SEQUENCE DESCRIPTION: SEQ ID NO:19:

```
GTAGAATGTC ATCCGTATTT CAACCGGAGT AAATTGCTAG ATTTCTGCAA GTCGAAAGAT      60

ATTGTTCTGG TTGCCTATAG TGCTCTGGGA TCTCAACGAG ACAAACGATG                110
```

(2) INFORMATION FOR SEQ ID NO:20:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

```
GTAATAAAAA CAATGGGACC TTTACATAAA CCTTCATTTT GCAGAAAATT TTTTAGTCAG      60

AGCATCCTCA GTTTCCTGTA GTTAAGTTTC AAGTGGCTCA TGGAGAGGAA AGAGAATTGC     120

GTTTCTGACG AGATCT                                                     136
```

(2) INFORMATION FOR SEQ ID NO:21:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

```
TTTAGGGAGC TGCCTAACAA ACTATCGGCA GCCTCAGGGC CTCAGCCTTT CTGCCTTTCC      60

TTCCAG                                                                 66
```

(2) INFORMATION FOR SEQ ID NO:22:

(i) SEQUENCE CHARACTERISTICS:
            (A) LENGTH: 166 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: exon
            (B) LOCATION: 1..166

(xi) SEQUENCE DESCRIPTION: SEQ ID NO:22:

GGTGGACCCG AACTCCCCGG TGCTCTTGGA GGACCCAGTC CTTTGTGCCT TGGCAAAAAA        60

GCACAAGCGA ACCCCAGCCC TGATTGCCCT GCGCTACCAG CTGCAGCGTG GGGTTGTGGT       120

CCTGGCCAAG AGCTACAATG AGCAGCGCAT CAGACAGAAC GTGCAG                     166

(2) INFORMATION FOR SEQ ID NO:23:

(i) SEQUENCE CHARACTERISTICS:
            (A) LENGTH: 136 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

GTGAGGAGCG GGGCTGTGGG CCTCAGGTCT CCTGCACAGT GTCCTTCACA CGTGTGCTTC        60

TTGTAAGGCT CTCAGGACAG CCTTGGGCCA GCTCCATTTC CCTGTATTTC CCATATGAAT       120

GCTTTGCGTG CATCCT                                                      136

(2) INFORMATION FOR SEQ ID NO:24:

(i) SEQUENCE CHARACTERISTICS:
            (A) LENGTH: 286 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

CCCTATCATG TGGGCACAAT GTCAGCGCTG TTTCTTCTCC ATTTTCTGTT GAAATTTTCT        60

CTTTGTCTGC AGAGTTGCAC AGTTTCAATA CATAATATCT AGGAATGGAT TTCTGCTTAT       120

TTTTCGTGAG CTATTCATTG ACCCACCTGA GTGTTTAGAG CTGACTTCTA TAACTGTTTA       180

AAACTTACCA ATATTTTAAG TATTGTCTCT GCACCCTACT GTCTAATATA CTTGGGGATT       240

CACAACTGGC AATCTAAAAA TAATAAAAGT TTTTTATTTC TGATAG                     286

(2) INFORMATION FOR SEQ ID NO:25:

(i) SEQUENCE CHARACTERISTICS:

(A) LENGTH: 83 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 1..83

(xi) SEQUENCE DESCRIPTION: SEQ ID NO:25:

GTTTTTGAGT TCCAGTTGAC TGCAGAGGAC ATGAAAGCCA TAGATGGCCT AGACAGAAAT      60

CTCCACTATT TTAACAGTGA TAG                                              83

(2) INFORMATION FOR SEQ ID NO:26:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

GTAAGTTTCC TTTGTAAATG GGTGATCTAA TTTATTTCTG GAGAAGGAAT GTAGGATGGG      60

TGTTGAGAGT GACCTCCATA CCAGAGGGAC AGAGGCCAAT GTGAGTCAGA GGTGAGACTG     120

GAACTCTCCT GCTGGATTCA CTCCAGAGCT CTGTTCTCTG GCAGGGTGAG TGGGCAGGGA     180

TCAGCATGGG TCAACCTGTG CCTCTGCTCT CCTGACTCCA TGGAACTTTC CAGAGCAGCC     240

AACATCATTG CCAAGTCTGC ACGTTCCATA TAGGCCTGGT GTTTCTACCA CTGGACATGC     300

TGTGGATACT GCCCATGTGA CTTCATTAGA TGTTTCCAAA TCTGTGCTTA TATCACATTG     360

TCCCAAACCT GCTCAGCTCC TTATCAAATC AAAAACATTT CCATCAACTT TGTGGTCCAG     420

GTGCCAATTC CCACCTCCTT CATATGGAAT TGCTTGCTAG ATCCTGTCAA TTCAGCATCT     480

TTTATTATTT CAAATGTTTT TCCTCCTTCT CCTTGCACGT TTGTTCATGC CCCAAACTCT     540

GCTTTTGCCT CCAGAAAGCC TTCCTTAGTG GAGTGAATAG GAGTGCTTGT CCTTGATTTC     600

CTGCAATATG GAGCTCTCAA GGCAGAGAAT TTAAAAAAAT TTAAAATCAA GGAGTGTGAG     660

TGTGGAGGCA GAAGCTCCAT TGTTGTATAT AATTTGTAGC TGATAAAAGA TCT            713

(2) INFORMATION FOR SEQ ID NO:27:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

```
TTTAATGCAC TGTAGCTCCT TGGATATTAG ACCCTATATC ATATATAACA ATTTACATTT      60

CTGAATCTTA CAAAATATAT TGCATACAGT AGGCAGTAGC AGGTAATAAG TAAAGTAACA     120

AAAGAAAGTA TAATCAGAGT ATCTCTGCTC TGCTGACAGA TGTACAGGAA TATACTTGAA     180

TATTTGACTT TGTGTGTTTT ACGTGTTAAC TTCCAGATAA GGGAATATGA TTGAATAATT     240

TATTATTTTG AAAATACTGT ATTATGAAGC CATGTTCATA AAGGTAAGAA AGGCAGATTC     300

TACAACTAGT CAGACAACTT AACATTCATA CTAATGACAG CTTCATTGAA ATCACTTTAC     360

TACTCCCCTA GTAATGGAGT CATTGCATTT ATATTATACA TTATTCTCTT TTCAG         415
```

(2) INFORMATION FOR SEQ ID NO:28:

(i) SEQUENCE CHARACTERISTICS:
        (A) LENGTH: 230 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 1..230

(xi) SEQUENCE DESCRIPTION: SEQ ID NO:28:

```
TTTTGCTAGC CACCCTAATT ATCCATATTC AGATGAATAT TAACATGGAG GGCTTTGCCT      60

GATGATGTCT ACCAGAAGGC CCTGTGTGTG GATGGTGACG CAGAGGACGT CTCTATGCCG     120

GTGACTGGAC ATATCACCTC TACTTAAATC CGTCCTGTTT AGCGACTTCA GTCAACTACA     180

GCTGAGTCCA TAGGCCAGAA AGACAATAAA TTTTTATCAT TTGAAATAA                 230
```

(2) INFORMATION FOR SEQ ID NO:29:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:29:

```
TTGAATGTTT TCTCAAAGAT TCTTTACCTA CTCTGTTCTG TAGTGTGTGT TTTCTTCTGG      60

CTCAGAAGTG TGTGTGTGTG TGTGTGTGCT TTCTTCTGGC TCAACAGGG                109
```

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:30:

TTTAGCTTTA CACACTGCTG TT                                                     22

(2) INFORMATION FOR SEQ ID NO:31:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:31:

TCCAAAGCTT TACTTCTCGG                                                        20

(2) INFORMATION FOR SEQ ID NO:32:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:32:

GATGAAAAGT GGACCA                                                            16

(2) INFORMATION FOR SEQ ID NO:33:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:33:

ATCTGTTGGT GAAAGTTC                                                          18

(2) INFORMATION FOR SEQ ID NO:34:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:34:

TCCAGCTGCC TGCGGT                                                            16

(2) INFORMATION FOR SEQ ID NO:35:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:35:

CTTGTACTTG AGTCCTG                                                17

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:36:

CTCCGGTTGA AATACGGA                                            18

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:37:

CATCGTTTGT CTCGTTGAGA                                       20

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:38:

TCACTGTTAA AATAGTGGAG AT                                    22

(2) INFORMATION FOR SEQ ID NO:39:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:39:

ATCTGAATAT GGATAAT                                                   17

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:40:

TTCTCGGAAC CTGGAGGAGC                                                20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:41:

GACACAGTAC CTTTGAAGTG                                                20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:42:

TGGACCAAAG CTGCAGAGGT                                                20

(2) INFORMATION FOR SEQ ID NO:43:

(i) SEQUENCE CHARACTERISTICS:
        (A) LENGTH: 20 base pairs

```
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:43:

CCTCACCTGG CTGAAATAGA                                           20

(2) INFORMATION FOR SEQ ID NO:44:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:44:

AAGCACTCAC CTCCCAGGTG                                           20

(2) INFORMATION FOR SEQ ID NO:45:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:45:

GACATTCTAC CTGCAGTTGA                                           20

(2) INFORMATION FOR SEQ ID NO:46:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:46:

CTCAAAAACC TATCAGAAA                                            19

(2) INFORMATION FOR SEQ ID NO:47:

(i) SEQUENCE CHARACTERISTICS:
            (A) LENGTH: 20 base pairs
            (B) TYPE: nucleic acid
            (C) STRANDEDNESS: single
            (D) TOPOLOGY: linear
```

(ii) MOLECULE TYPE: DNA (genomic)

(iii) HYPOTHETICAL: NO (iv) ANTI-SENSE: YES (xi) SEQUENCE DESCRIPTION: SEQ ID NO:47:

GGAAACTTAC CTATCACTGT                                                    20

(2) INFORMATION FOR SEQ ID NO:48:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:48:

GCTAGCAAAA CTGAAAAGAG                                                    20

(2) INFORMATION FOR SEQ ID NO:49:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:49:

GAGAAATATT CATTCTG                                                       17

(2) INFORMATION FOR SEQ ID NO:50:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:50:

CGAGTCCTGA TAAAGCTG                                                      18

(2) INFORMATION FOR SEQ ID NO:51:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:51:

GATGAGGGTG CAAATAA                                                          17

(2) INFORMATION FOR SEQ ID NO:52:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:52:

GGAGTGTTAA TTAATAACAG TTT                                                   23

(2) INFORMATION FOR SEQ ID NO:53:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:53:

CAGAGATTAC AAAAACAAT                                                        19

(2) INFORMATION FOR SEQ ID NO:54:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:54:

TGCCTTTTTA CATTTTCAAT CA                                                    22

(2) INFORMATION FOR SEQ ID NO:55:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:55:

ACACATAATT TAAAGGA                                                          17

(2) INFORMATION FOR SEQ ID NO:56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:56:

TTAAATTATT CAAAAGG                                                          17

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:57:

AAGAGAAATA TTCATTTCTG                                                       20

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:58:

CCCCTCCCCC CACCCCTGCA                                                       20

(2) INFORMATION FOR SEQ ID NO:59:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:59:

-continued

| CTGCCGTGAT AATGCCCC | 18 |